United States Patent
Cady et al.

(10) Patent No.: US 8,715,711 B2
(45) Date of Patent: May 6, 2014

(54) LONG-ACTING INJECTABLE MOXIDECTIN FORMULATIONS AND NOVEL MOXIDECTIN CRYSTAL FORMS

(71) Applicants: Susan Mancini Cady, Yardley, PA (US); Baoqing Ma, Kendall Park, NJ (US); Robert Clark Chapman, Downingtown, PA (US); Chunhua Yang, Edison, NJ (US); Uday Jain, Plainsboro, NJ (US)

(72) Inventors: Susan Mancini Cady, Yardley, PA (US); Baoqing Ma, Kendall Park, NJ (US); Robert Clark Chapman, Downingtown, PA (US); Chunhua Yang, Edison, NJ (US); Uday Jain, Plainsboro, NJ (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 13/690,185

(22) Filed: Nov. 30, 2012

(65) Prior Publication Data

US 2013/0143956 A1    Jun. 6, 2013

Related U.S. Application Data

(60) Provisional application No. 61/566,336, filed on Dec. 2, 2011.

(51) Int. Cl.
*A61F 2/02* (2006.01)
*A61K 9/14* (2006.01)

(52) U.S. Cl.
USPC ............................ 424/426; 424/486; 514/953

(58) Field of Classification Search
USPC .................... 514/450, 953; 264/15; 549/264; 424/426, 486
See application file for complete search history.

(56) References Cited

U.S. PATENT DOCUMENTS

| | | | |
|---|---|---|---|
| 4,900,753 A | 2/1990 | Sutherland et al. |
| 4,916,154 A | 4/1990 | Asato et al. |
| 4,988,824 A | 1/1991 | Maulding et al. |
| 5,106,994 A | 4/1992 | Carter et al. |
| 5,837,228 A | 11/1998 | Shih et al. |
| 6,162,820 A | 12/2000 | Jeannin et al. |
| 7,645,863 B2 | 1/2010 | Sorokin et al. |

FOREIGN PATENT DOCUMENTS

EP          1 505 069 A1     2/2005

OTHER PUBLICATIONS

Beddall NE et al. Chemical transformations of S541 factors (A)-(D): preparation and reactions of the 23-ketones. Tetrahedron Letters. V29; N21. Jan. 1, 2998 [Cited in ISR for instant applic.], 1988.
Clark SL et al. "Long-term delivery of ivermectin by use of poly(D,L-lactic-co-glycolic)acid microparticles in dogs." AJVR, vol. 65, No. 6, Jun. 2004.
Fort Dodge Animal Health Bulletin/Brochure/RiskMap. ProHeart 6. May 2008 (exact publication date unknown).
Genchi et al. "Efficacy of moxidectin microsphere sustained release formulation for the prevention of subcutaneous filarial (*Dirofilaria repens*) infection in dogs." Veterinary Parasitology 170 (2010) 167-169.
Ley SV and Armstrong A. Chapter 7: "The Champagne route to avermectins and milbemycins." Strategies and Tactics in Organic Synthesis, vol. 3. 1991.
Cobb & Boeckh. Moxidectin: a review of chemistry, pharmacokinetics and use in horses. A. Parasites and Vectors 2009, 2 (Suppl 2) S5.
Carter et al. LL-F28249 Antibiotic Complex: A New Family of Antiparasitic Macrocyclic Lactones. Journal of Antibiotics. vol. XLI No. 4, 1987.

*Primary Examiner* — Kristin Vajda
(74) *Attorney, Agent, or Firm* — Judy Jarecki-Black; Chad Kitchen; Merial Limited

(57) ABSTRACT

This invention provides for novel antiparasitic and pesticidal forms of moxidectin, including a long-acting polymeric implant. The resulting compounds may be used in veterinary compositions which are used in treating, controlling and preventing of endo- and ectoparasite infections in animals.

14 Claims, 33 Drawing Sheets

PRXD of Moxidectin lot S090601

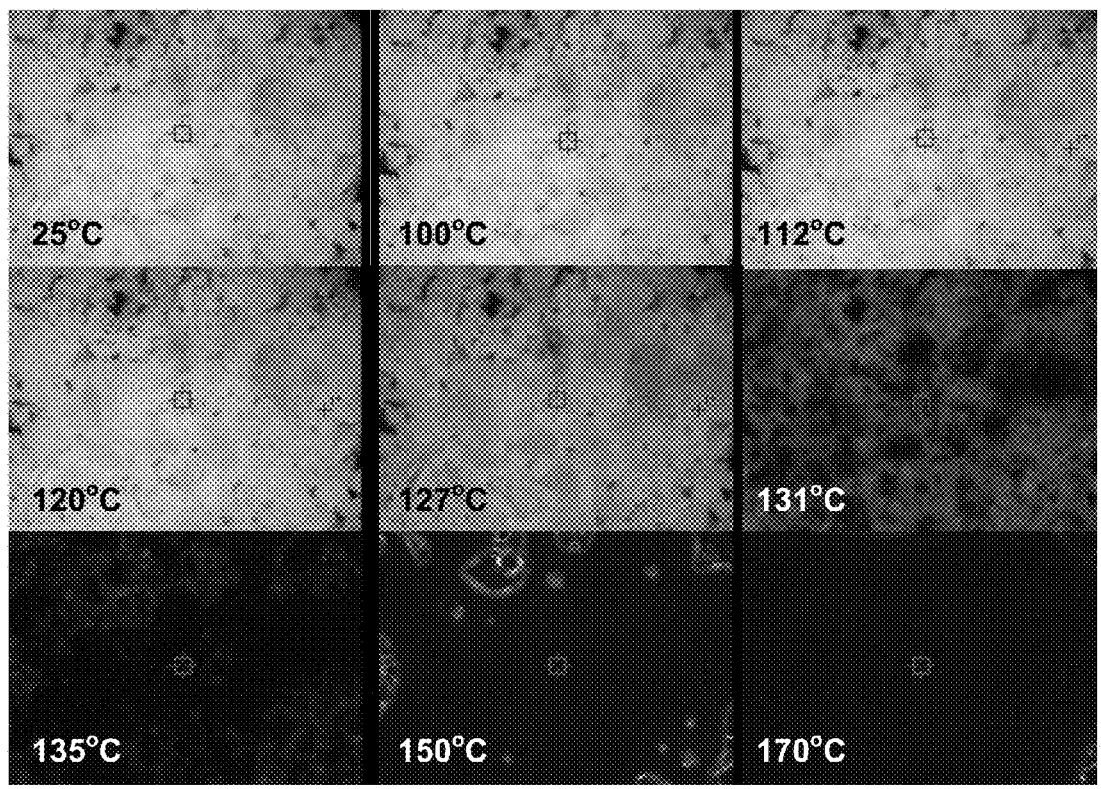

FIG. 11 (2/2)
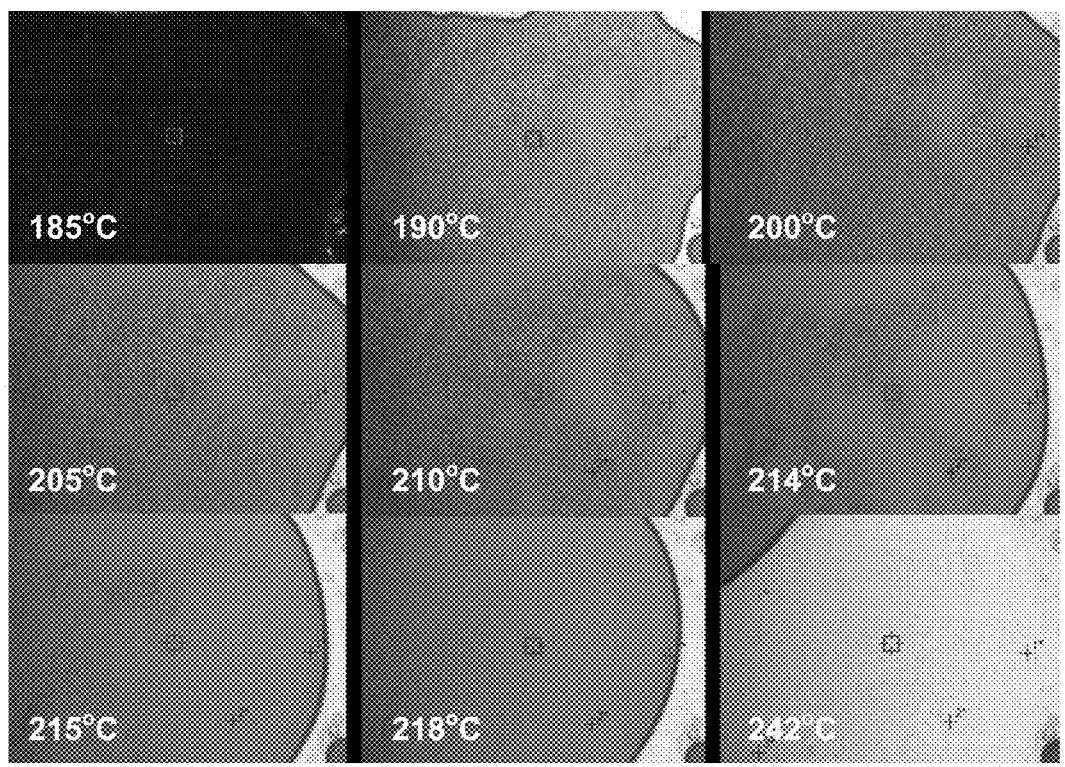

Wavelength: 1.54056    2 theta    32.928, 9793   h, k, l = 3, 2, -3

FIG. 42
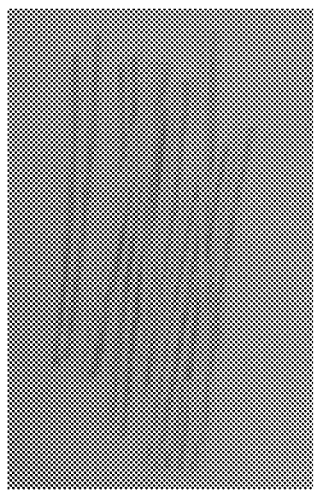
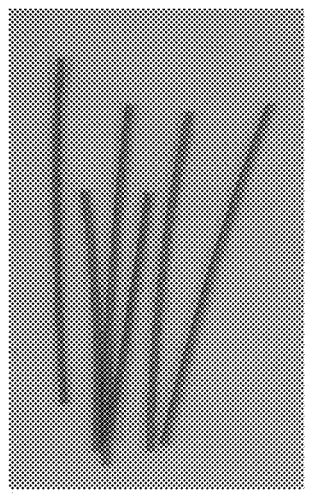
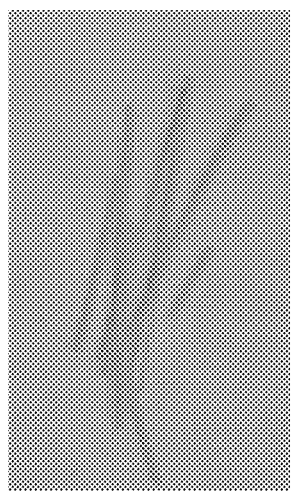
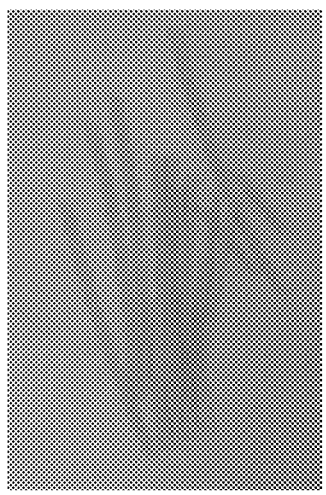
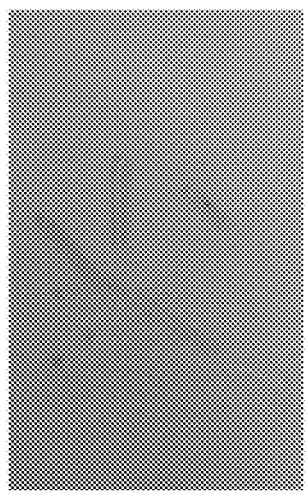

LONG-ACTING INJECTABLE MOXIDECTIN FORMULATIONS AND NOVEL MOXIDECTIN CRYSTAL FORMS

CROSS-REFERENCE TO RELATED APPLICATIONS

This application claims benefit of U.S. Provisional Application No. 61/566,336, filed on Dec. 2, 2011, and incorporated herein by reference.

FIELD OF THE INVENTION

This invention relates to novel antiparasitic polymorphs and solvates (pseudopolymorphs) of moxidectin, as well as methods for producing same. The novel moxidectin forms may be used in oral, parental or topical veterinary formulations for treating, controlling and preventing of endo- and ectoparasite infections/infestations in mammals, birds or fish, such as horses and household pets. The invention further relates to the use of these forms in novel parasiticidal moxidectin polymeric formulations, which may be administered to animals, including dogs and cats, for long-acting control of endoparasites, including heartworms. The present invention also relates to methods of controlling release of a beneficial agent from a formulation and methods of using the formulation to administer a beneficial agent to an animal.

BACKGROUND OF THE INVENTION

Animals and humans suffer from endoparasitical infections including, for example, helminthiasis which is most frequently caused by a group of parasitic worms described as nematodes or roundworms. These parasites cause severe economic losses in pigs, sheep, horses, and cattle as well as poultry. Other parasites which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

Because of bioavailability, efficacy, or dosing convenience concerns, many beneficial agents are preferably administered parenterally. Since a recipient could receive several dosage forms over a lifetime, it is essential that the dosage form leave little or no undesirable residue. Bioerodible polymeric dosage forms are ideally suited for these applications, and provide the additional advantage that drug delivery from a single dosage form may effectively treat the disease state for a prolonged period.

Known bioerodible polymeric controlled release devices can be generally categorized as either encapsulated devices or matrix devices. In encapsulated devices, beneficial agent (e.g., drug) is surrounded by a polymer layer which controls release of the beneficial agent. The beneficial agent in a matrix device, however, is dissolved or suspended in the polymer matrix and diffuses through the matrix, or is released in conjunction with the dissolution, disintegration, decomposition, or erosion of the matrix.

With matrix devices, beneficial agents can be incorporated into the matrix by physical entrapment or are chemically bound to the matrix. When exposed to a biological environment of use, the polymer matrix dissolves, disintegrates, decomposes, or erodes (i.e., degrades) to release beneficial agent. Significant experimental effort is required to "tune" the polymer/beneficial agent formulation to enable it to be stable and to release at the desired rate.

As regards treatment and prevention of parasitic infestation, a particularly important class of beneficial agents is the macrocyclic lactone, which may be used for treating endo- and ectoparasite infections in mammals and birds. Compounds that belong to this class include the avermectins and milbemycins. These compounds are potent antiparasitic agents against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, avermectins and milbemycins are used to treat endoparasites, e.g., round worm infections, in warm-blooded animals.

The avermectins may be isolated from the fermentation broth of an avermectin producing strain of *Streptomyces avermitilis* and derivatives thereof. The production, isolation and structural determination of the avermectins are documented in Albers-Schonberg, et. al, *J. Am. Chem. Soc.* 1981, 103, 4216-4221 and references cited therein. The description of the morphological characteristics of the culture is described in U.S. Pat. No. 4,310,519, which is incorporated herein by reference.

The milbemycins are the aglycone derivatives of the avermectins, such as those described, for example in U.S. Pat. Nos. 4,144,352; 4,791,134; and 6,653,342. A particularly important anthelmintic of this family includes moxidectin, as described, for example in U.S. Pat. No. 7,348,417; U.S. Pat. No. 4,900,753; U.S. Pat. No. 4,988,824; U.S. Pat. No. 5,106,994; U.S. Pat. No. 7,645,863; and U.S. Pat. No. 4,916,154 (and references cited therein). For milbemycins, reference may be made, inter alia, to Vercruysse, J. and Rew, R. S., editors, *Macrocyclic Lactones in* Antiparasitic Therapy, CABI International 2002; Campbell, William C., editor, *Ivermectin and Abamectin*, Springer-Verlag, 1989; Davies H. G. et al., 1986, "Avermectins and Milbemycins", Nat. Prod. Rep., 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054. As evidenced by the numerous references, amorphous moxidectin is well-known in the art, but other solid forms, including crystalline polymorphs and solvates/hydrates (pseudopolymorphs), have not been described.

U.S. Pat. No. 6,162,820 (to Merial) disclosed long-acting combinations of fipronil and ivermectin (an avermectin).

U.S. Pat. No. 6,733,767 (to Merck) disclosed a liquid polymeric composition for controlled release of eprinomectin, consisting essentially of the active ingredient, PLGA, and solvent mixture. The composition forms a depot upon injection into the animal.

U.S. Pat. No. 6,797,701 (to Pfizer) disclosed avermectin 13-monosaccharide 5-oxime formulations consisting essentially of the active ingredient and glycol ether.

U.S. Pat. No. 7,326,428 (to Rutgers University) disclosed (in its background section) ivermectin encapsulated in PLGA (50:50) microspheres. The subsequent pulsed release of this agent, in vivo, was shown to be dependent on the degradation rate of the polymer matrix.

US 2004/0241204 (to Martinod et al.) disclosed sustained release mini-implants or pellets in combination may provide a blood level of ivermectin active preferably 1 to 4 weeks. A list of potential polymers was disclosed, including PLGA, polyamino acids, PGS and Biopol.

Ivermectin was also successfully combined with PLGA to produce a biodegradable drug delivery matrix for use in dogs (Clark et al., AJVR 2004).

ProHeart 6 (Pfizer sustained-release moxidectin product) provided moxidectin sterile microspheres, however, the product was recalled on Sep. 3, 2004 due to adverse events, including death, thus illustrating the significant challenge in producing formulations capable of safely delivering beneficial agents, particularly moxidectin, over long periods of time.

In view of above references, there are several examples of macrocyclic lactone "microsphere" formulations, as well as "liquid polymer depot-type" formulations, but inventors are unaware of any polymeric moxidectin solid implant dosage forms as of the filing of this disclosure.

All of these documents and references cited therein, as well as the references cited herein, are expressly incorporated by reference.

Notwithstanding the excellent progress in antiparasitic research, concerns remain with respect to increasingly common reports of resistance among veterinary parasites (*Parasitology* 2005, 131, S179-190). Other concerns related to potential adverse effects on dung-dwelling insects essential for dung degradation have been raised with respect to endectocides. Thus, there remains an ongoing need for novel endectocides and anthelmintic treatments in veterinary medicine. It is an object of this invention to provide novel endectocides and anthelmintic compounds and formulations, as well as methods of treatment using such compounds. That the invention performs as herein described is surprising, unexpected and nonobvious.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application does not constitute an admission that such document is available as prior art to the present invention.

SUMMARY OF THE INVENTION

The instant invention provides for, inter alia, novel crystalline forms of moxidectin, which are effective against endo- and ectoparasites that infest warm-blooded animals, including humans. Thus, it is an object of the invention to describe such novel solid forms.

In another aspect, the invention relates to pharmaceutical and/or veterinary compositions and methods of making and using the alternate forms of moxidectin. In one aspect, the moxidectin polymorph has a melting point of about 210° C.

In still another aspect, the invention also provides for methods for producing [moxidectin.butanol$_n$], [moxidectin.IPA$_n$], and [moxidectin.ethanol$_n$] solvates from amorphous moxidectin. In another aspect, the invention relates to methods for preparing the moxidectin polymorph comprising the general steps of, for example, but not solely, A) rapidly desolvating a [moxidectin.1.5 butanol] solvate; or B) heating amorphous moxidectin under specific conditions of temperature and time.

A second object of this invention is to provide for long-acting moxidectin-containing polymeric formulations, which are effective in preventing infestation of animals by endoparasites, including heartworms, for at least several months, and up to as long as six months, or more. Also disclosed are processes for producing the long-acting polymeric formulations. In an embodiment, a solution of moxidectin, optionally antioxidants including BHT, and poly d lactide-glycolide (from about 75:25 L:G to about 25:75 L:G) is produced in appropriate solvent, for example methylene chloride, and spray dried, followed by extrusion at about 118° C. In an embodiment, implantable pellets are cut from the resulting polymer strands.

A third object of this invention is to provide for methods of treatment of parasitic infections of animals, which comprise treating the infected animal with an effective antiparasitic and anthelmintic amount of the newly described forms of moxidectin or the long-acting polymeric formulations, or combinations thereof.

It is noted that the invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass avermectin/milbemycin or previously disclosed derivatives of avermectin/milbemycin.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which.

FIG. 11 presents microscopic images of hot-stage moxidectin (lot S090601);

FIG. 12 is an image of moxidectin crystal recrystallized from MeOH (moxidectin $(MeOH)_x$;

FIG. 13 presents the PXRD of air-dried moxidectin/MeOH crystals (moxidectin.$(MeOH)_x$;

FIG. 14 is a TGA of air-dried moxidectin/MeOH crystals;

FIG. 15. DSC of air-dried moxidectin/MeOH crystals;

FIG. 16 presents an image of Moxidectin crystal resulting from recrystallization of (lot S090601) from EtOH (amorphous form);

FIG. 17 presents the PXRD of air-dried moxidectin/EtOH crystals(moxidectin $(EtOH)_x$);

FIG. 18 presents the TGA of air-dried moxidectin/EtOH crystals;

FIG. 19 presents the DSC of air-dried moxidectin/EtOH crystals;

FIG. 20 presents the DSC of vacuum-dried moxidectin/EtOH crystals;

FIG. 21 presents the PXRD of moxidectin/EtOH crystals after vacuum drying at 95° C.;

FIG. 22 presents the molecular structure of moxidectin/EtOH showing its hydrogen bonding connection;

FIG. 23 presents a packing diagram showing its porous channels along [100] direction;

FIG. 24 presents an image of Moxidectin crystal resulting from recrystallization of (lot S090601)(amorphous) from IPA (moxidectin.$(iPrOH)_x$);

FIG. 25 presents the PXRD air-dried moxidectin/IPA crystals(moxidectin.$(iPrOH)_x$);

FIG. 26 presents an image of Moxidectin crystal recrystallized from IPA (lot 070201);

FIG. 27 presents the TGA of air-dried moxidectin/IPA crystals;

FIG. 28 presents the DSC of air-dried moxidectin/IPA crystals;

FIG. 29 presents the DSC of vacuum-dried moxidectin/IPA crystals;

FIG. 30 presents an image of Moxidectin crystal recrystallized from n-Butanol(moxidectin $(n\text{-}BuOH)_x$);

FIG. 31 presents the PXRD of air-dried moxidectin/n-Butanol crystals(moxidectin $(n\text{-}BuOH)_x$);

FIG. 32 presents the TGA of air-dried moxidectin/n-Butanol crystals;

FIG. 33 presents the DSC of air-dried moxidectin/n-Butanol crystals;

FIG. 34 presents the DSC of vacuum-dried moxidectin/n-Butanol crystals at 60° C.;

FIG. 35 presents the PXRD of moxidectin/n-Butanol crystals after vacuum drying at 65° C.;

FIG. 36 presents DSC of vacuum-dried moxidectin/n-Butanol crystals at RT (moxidectin $(n\text{-}BuOH)_x$);

FIG. 37 presents Image of Moxidectin crystal recrystallized from methylcyclohexane (moxidectin $(Ma)_x$);

FIG. 38 presents PXRD of air-dried moxidectin/MCH crystals(moxidectin $(MCH)_x$);

FIG. 39 presents TGA of air-dried moxidectin/MCH crystals;

FIG. 40 presents DSC of air-dried moxidectin/MCH crystals;

FIG. 41 presents An overlay of PXRD of air-dried moxidectin/MCH, moxidectin/MeOH and thermal transformed moxidectin;

FIG. 42 depicts polymeric implants according to the instant invention;

FIG. 43 depicts heat flow DSC for 2 different polymeric implants;

FIG. 44 presents in vitro release for a long-acting formulation (Lot 438-148) containing amorphous moxidectin, 75:25 DLG, 0.4 iv;

FIG. 45 presents in vitro release for a long-acting formulation (Lot 588-17) containing crystalline moxidectin (Form A), 75:25 DLG, 0.4 iv;

FIG. 46 presents moxidectin plasma levels for canines implanted with the amorphous moxidectin long-acting formulation.

DETAILED DESCRIPTION

The crystal forms of moxidectin of the invention and compositions comprising the forms are highly effective for the treatment or prophylaxis of parasites in or on mammals, fish and birds, and in particular, cats, dogs, horses, chickens, pigs, sheep and cattle with the aim of ridding these hosts of all the parasites commonly encountered by mammals, fish and birds.

The compounds and compositions of the invention are also active against pests that damage agricultural material, and may be effectively used to treat and protect plants, crops, plant propagation material, property containing wood or derived from wood, from harmful pests.

Accordingly, the present invention provides methods for preventing and treating parasites in or on animals, comprising administering a parasiticidally effective amount of a novel moxidectin form to the animal. The invention also provides a method for combating or controlling pests and for protecting crops, growing plants, plant propagation material, and wood-containing material, or material derived from wood, from infestation by pests, comprising contacting the pests, plants, plant propagation material, or the soil or water in which the plants is growing, or the wood-containing material or material derived from wood, with a pesticidally effective amount of the novel moxidectin forms.

As used herein, the following terms have the meanings ascribed to them unless specified otherwise. In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless otherwise specifically noted or apparent by context, "active agent" or "active ingredient" or "therapeutic agent" as used in this specification, means moxidectin, including, but not limited to, amorphous, crystalline and solvate/hydrate forms.

One embodiment of the second object of the invention provides a composition useful for the treatment or prevention of a parasitic infection in an animal which comprises an inert carrier and an effective amount of a form of moxidectin.

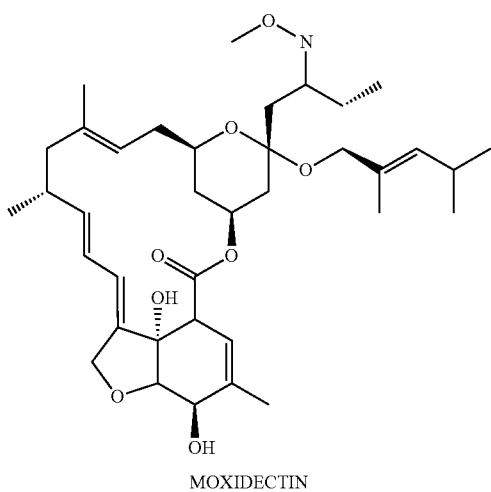

MOXIDECTIN

The invention also provides compositions useful for combating or controlling pests and for protecting crops, growing plants, plant propagation material, and wood-containing material, or material derived from wood from infestation by pests, comprising a pesticidally effective amount of a form of moxidectin, in combination with an agriculturally acceptable carrier.

One embodiment of the third object of the invention provides for a method for the treatment or prevention of parasitic infections/infestations of animals, which comprises administering an effective amount of a compound of formula (I) to the animal in need thereof.

In still another embodiment of the invention, a method is provided for the treatment or prevention of a parasitic infestation at a locus, which comprises administering or applying a parasiticidally effective amount of moxidectin, or pharmaceutically acceptable salts thereof, to the locus. With respect to animal health applications, "locus" is intended to mean a habitat, breeding ground, area, material or environment in which a parasite is growing or may grow, including in or on an animal.

Still further embodiments of the objects of the invention will become apparent as described herein.

The forms and solvates of formula (I) are prepared by the application or adaptation of known methods (i.e. methods heretofore used or described in the chemical literature); or methods described in one or more of U.S. Pat. Nos. 4,199,569; 4,310,519; 4,423,209; 4,427,663; 4,457,920, 4,806,527; 4,831,016; 4,855,317; 4,859,657; 4,871,719; 4,873,224; 4,874,749; 4,895,837; 4,906,619, 4,920,148; 4,963,582; 4,973,711; 4,978,677; 5,015,630, 5,023,241; 5,030,622; 5,055,454; 5,055,596; 5,057,499; 5,077,308; 5,089,490; 5,162,363; 5,169,839; 5,208,222; 5,244,879; 5,262,400; 5,830,875; 7,250,402; and EP 0 214 731, all of which are incorporated herein by reference in their entirety. It will be appreciated by persons skilled in the art that the order of synthetic transformations employed may be varied, and will depend on factors such as the nature of other functional groups present in a particular substrate, the availability of key intermediates, and the protecting group strategy to be adopted.

Figure 1:
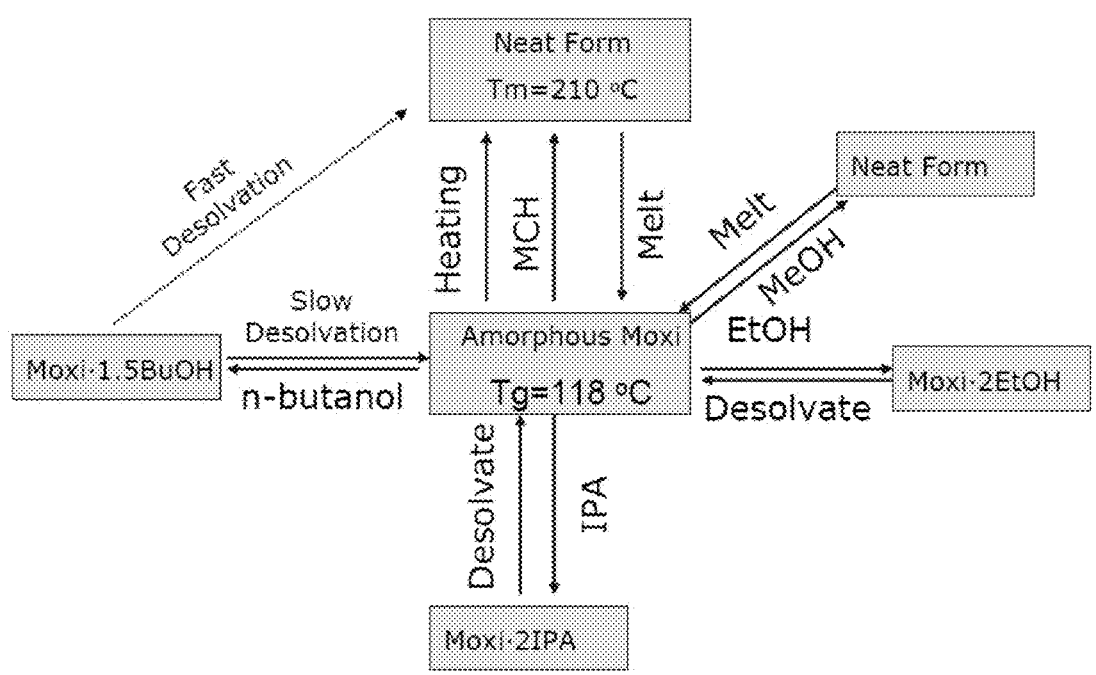
FIG. 1 depicts a flow diagram summarizing the disclosed moxidectin crystal forms and transformations to and therefrom.

In one embodiment of the invention, the moxidectin forms may be produced according to the procedures summarized in FIG. 1.

Figure 2A:
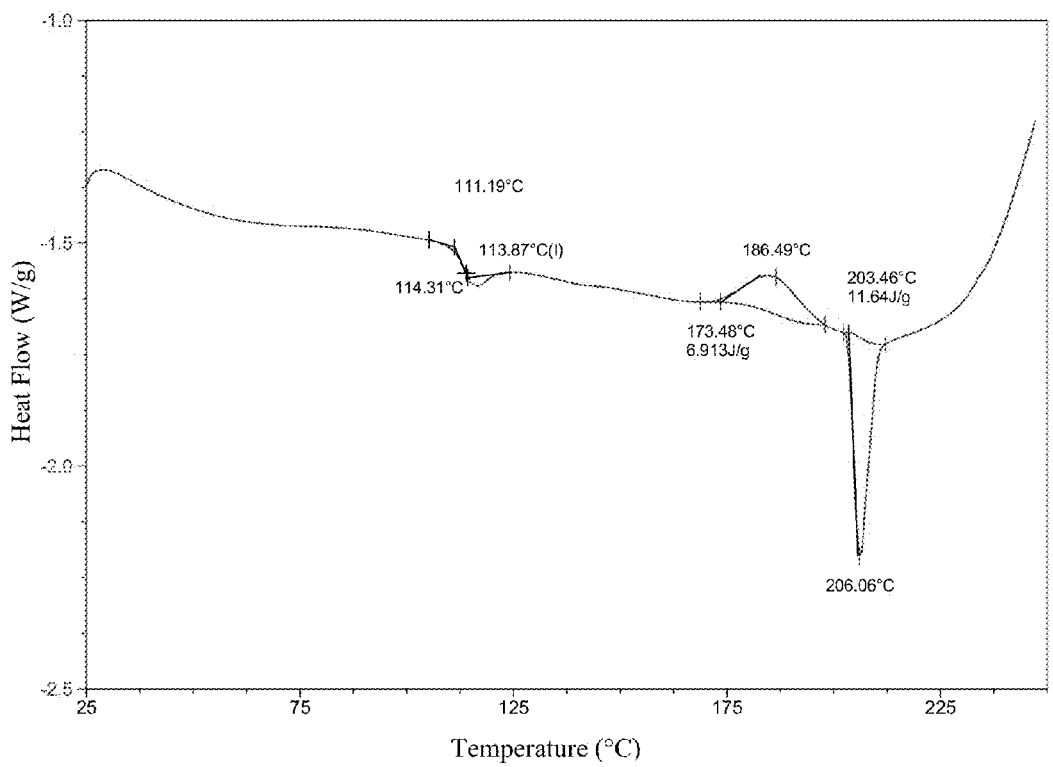
FIG. 2A depicts a DSC of moxidectin (lot S090601, amorphous form)
Figure 2B:
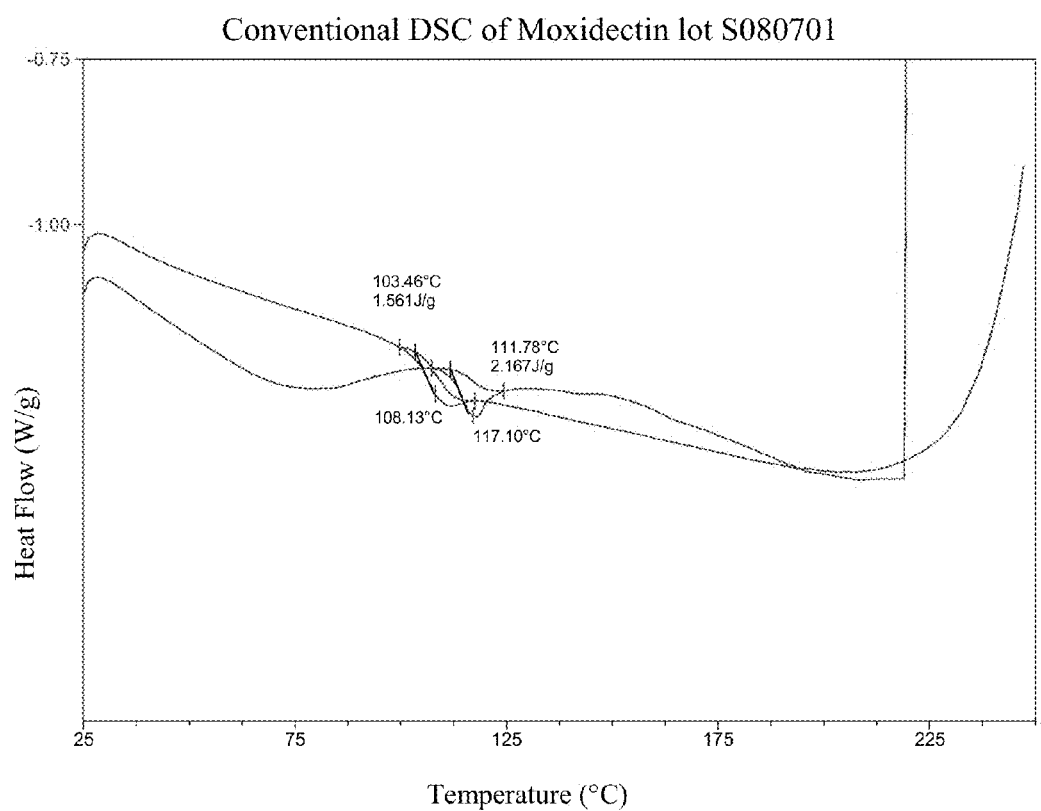
FIG. 2B depicts a DSC of moxidectin (lot S080701, amorphous form)

In another embodiment of the invention, the amorphous moxidectin is converted to the new crystalline form by immersing the moxidectin into an oil bath at 190° C. for about 2 to about 10 minutes, followed by cooling. Amorphous moxidectin may be distinguished from the novel crystalline moxidectin (Polymorph A), for example, by x-ray crystallography (FIG. 2A).

In an embodiment, with increasing temperature, amorphous moxidectin exhibits a glass transition at 115° C., crystallizes at 175° C. to Polymorph A, melts at 206° C., and finally decomposes at 230° C. Molten moxidectin becomes amorphous upon cooling. Moxidectin (lot 090601) crystallized at 175° C., and moxidectin (lot 080701) did not crystallize.

Terms used herein will have their customary meaning in the art unless specified otherwise. The organic moieties mentioned in the definitions of the variables of formula (I) are— like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. It also includes an individual animal in all stages of development, including embryonic and fetal stages.

The term "plant propagation material" refers to any parts of a plant which are propagable. In general, a plant propagation material includes the product of the ripened ovule of gymnosperm and angiosperm plants which occurs after fertilization and some growth within the mother plant and includes seed, fruits, spurious fruits, infructescences and also rhizomes (rootstocks), corms, tubers, bulbs and scions.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

A pharmaceutically acceptable carrier is selected on the basis of the form of the composition which can include oral formulations, baits, dietary supplements, powders, shampoos, pastes, concentrated solution, suspension, microemulsion and emulsion. Compositions intended for pharmaceutical use may be prepared according to any method known in the art for the manufacture of pharmaceutical compositions. Remington—The Science and Practice of Pharmacy ($21^{st}$ Edition) (2005), Goodman & Gilman's The Pharmacological Basis of Therapeutics ($11^{th}$ Edition) (2005) and Ansel's Pharmaceutical Dosage Forms and Drug Delivery Systems ($8^{th}$ Edition), edited by Allen et al., Lippincott Williams & Wilkins, (2005).

The composition of the invention can be in a variety of forms which include, but are not limited to, oral formulations, injectable formulations, and topical, dermal or subdermal formulations.

The composition of the invention may be in a form suitable for oral use, for example, as baits (see, e.g., U.S. Pat. No. 4,564,631 incorporated herein by reference), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, all of which are incorporated herein by reference, to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889, both of which are incorporated herein by reference. In addition to the active agent of the invention, the paste can also contain fumed silica; a viscosity modifier; a carrier; optionally, an absorbent; and optionally, a colorant, stabilizer, surfactant, or preservative.

The process for preparing a paste formulation typically comprises the steps of:
(a) dissolving or dispersing the active agent into the carrier by mixing;
(b) adding the fumed silica to the carrier containing the dissolved active agent compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride.

The paste may also include a viscosity modifier including, but not limited to, polyethylene glycols (PEG) such as PEG 200, PEG 300, PEG 400, PEG 600; monoethanolamine, triethanolamine, glycerol, propylene glycol, polyoxyethylene (20) sorbitan mono-oleate (polysorbate 80 or TWEEN 80), and polyoxamers (e.g., PLURONIC L 81); an absorbent selected from the group consisting of magnesium carbonate, calcium carbonate, starch, and cellulose and its derivatives.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

As vehicle or diluent, mention may be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent will be added. One embodiment of the emollient and/or spreading and/or film-forming agents are those agents selected from the group consisting of:
(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil,
(b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil),
(c) cationic surfactants such as water-soluble quaternary ammonium salts of formula $N^+R'R''R'''R''''Y^-$, in which the R radicals are optionally hydroxylated hydrocarbon radicals and $Y^-$ is an anion of a strong acid such as the halide, sulphate and sulphonate anions; cetyltrimethylammonium bromide is among the cationic surfactants which can be used,
(d) amine salts of formula $N^+R'R''R'''$ in which the R radicals are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine, and (g) a mixture of at least two of these agents.

The solvent will be used in proportion with the concentration of the active agent compound and its solubility in this solvent. Typically, it will be sought to have the lowest possible volume. The vehicle makes up the difference to 100%.

In one embodiment of the amount of emollient, the emollient may be used in a proportion of from about 0.1 to about 10%, and about 0.25 to about 5%, by volume.

The formulation can also comprise an antioxidizing agent intended to inhibit oxidation in air, this agent typically being present in a proportion of about 0.005 to about 1% (w/v), and about 0.01 to about 0.05% (w/v) being specially preferred.

In one embodiment of the antioxidizing agents, the agents are those conventional in the art and include, but are not limited to, butylated hydroxyanisole, butylated hydroxytoluene, ascorbic acid, sodium metabisulphite, propyl gallate, sodium thiosulphate or a mixture of not more than two of them.

The formulation adjuvants are well known to the practitioner in this art and may be obtained commercially or through known techniques. These concentrated compositions are generally prepared by simple mixing of the constituents as defined above. Advantageously, the starting point is to mix the active material in the main solvent and then the other ingredients or adjuvants are added.

Additionally, the inventive formulations may contain other inert ingredients such as antioxidants, preservatives, or pH stabilizers. These compounds are well known in the formulation art. Antioxidant such as an alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred. Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate. Preferred ranges for pH include from about 4 to about 6.5.

In one embodiment of the invention, the active agent is present in the formulation at a concentration of about 0.05 to about 60% (w/v). In another embodiment of the invention, the active agent is present in the formulation as a concentration from about 1 to about 50% or about 35 to about 50% (w/v). In yet another embodiment of the invention, the active agent is present in the formulation as a concentration from about 50% (w/v). In still another embodiment of the invention, the active agent is present in the formulation as a concentration about 35% (w/v), about 45% (w/v) or about 50% (w/v).

In one embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

The composition containing the active agent of the invention may be administered continuously, for treatment or prophylaxis, by known methods. Generally, a dose of from about 0.001 to about 100 mg per kg of body weight given as a single dose or in divided doses, for a period of days, weeks, or months, though higher or lower dosage ranges are indicated, and such are within the scope of this invention. It is well within the routine skill of the practitioner to determine a particular dosing regimen for a specific host and parasite.

In one embodiment, the treatment is carried out so as to administer to the animal, on a single occasion, a dose containing between about 0.001 and about 100 mg/kg of the active agent.

In another embodiment, the treatment is via a direct topical administration such as a paste, pour-on, ready-to-use, spot-on, etc. type formulation. Higher amounts may be provided for very prolonged release in or on the body of the animal. In another embodiment, the amount of the active ingredient for birds and animals which are small in size is greater than about 0.01 mg/kg, and in another embodiment for the treatment of small sized birds and animals, the amount of the active agent is between about 1 and about 100 mg/kg of weight of animal.

Other routes of administration include paste, chewable, and gel formulations.

The solid forms of the invention can be formulated in various ways, depending on the prevailing biological and/or chemico-physical parameters. Examples of possible formulations are: wettable powders (WP), water-soluble powders (SP), water-soluble concentrates, emulsifiable concentrates (EC), emulsions (EW) such as oil-in-water and water-in-oil emulsions, suspension concentrates (SC), dispersions on an oil or water basis, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Additional pharmaceutical active agents may be used in the compositions of the invention. Active agents include pesticidally or veterinarily active ingredients, which include, but are not limited to, acaricides, anthelmintics, anti-parasitics and insecticides, may also be added to the compositions of the invention. Anti-parasitic agents can include both ectoparasiticidal and endoparasiticidal agents.

Other active agents that are well-known in the art may be used in the compositions of the invention (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) including, but are not limited to, acarbose, acepromazine maleate, acetaminophen, acetazolamide, acetazolamide sodium, acetic acid, acetohydroxamic acid, acetylcysteine, acitretin, acyclovir, albendazole, albuterol, alfentanil, allopurinol, alprazolam, altrenogest, amantadine, amikacin, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine HCl, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone HCl, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, *propionibacterium acnes* injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, e.g. fipronil, are known in the art and are suitable for combination with the compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (each assigned to Merial, Ltd., Duluth, Ga.).

In another embodiment of the invention, one or more macrocyclic lactone(s) (in addition to the moxidectin) that are described above, which act as an acaricide, anthelmintic agent and insecticide, can be added to the compositions of the invention. The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference, both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2, 6-difluorobenzoyl)-3-(2-fluoro-4-(trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analog may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion-diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3 a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are incorporated herein by reference. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In a further aspect, the invention relates to a method of treating livestock to prevent or decrease the level of infection by endo- and/or ecto-parasites, which may comprise administering to the livestock an anti-parasitic formulation as described herein.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus.*

In another embodiment of the invention, the compounds and compositions of the invention are suitable for controlling pests such as insects selected from the group consisting of *Blattella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonolaimus* spp., *Bursaphelenchus* spp., *Ditylenchus dipsaci, Globodera* spp., *Helicotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:
(1) from the order of Isopoda, for example *Oniscus asellus, Armadillidium vulgare* and *Porcellio scaber;*
(2) from the order of Diplopoda, for example *Blaniulus guttulatus;*
(3) from the order of Chilopoda, for example *Geophilus carpophagus* and *Scutigera* spp.;
(4) from the order of Symphyla, for example *Scutigerella immaculata;*
(5) from the order of Thysanura, for example *Lepisma saccharina;*
(6) from the order of Collembola, for example *Onychiurus armatus;*
(7) from the order of Blattaria, for example *Blatta orientalis, Periplaneta americana, Leucophaea maderae* and *Blattella germanica;*
(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;
(10) from the order of Anoplura (Phthiraptera), for example, *Damalinia* spp., *Haematopinus* spp., *Linognathus* spp., *Pediculus* spp., *Trichodectes* spp.;
(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyp hagotarsonemus latus, Psoroptes* spp., *Rhipicephalus* spp., *Rhizoglyphus* spp., *Sarcoptes* spp., *Scorpio maurus, Steneotarsonemus* spp., *Tarsonemus* spp., *Tetranychus* spp., *Vasates lycopersici;*
(12) from the class of Bivalva, for example, *Dreissena* spp.;
(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceutorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;
(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;
(15) from the class of Gastropoda, for example, *Anion* spp., *Biomphalaria* spp., *Bulinus* spp., *Denocenas* spp., *Galba* spp., *Lymnaea* spp., *Oncomelania* spp., *Succinea* spp.;
(16) from the class of helminths, for example, *Ancylostoma duodenale, Ancylostoma ceylanicum, Ancylostoma braziliensis, Ancylostoma* spp., *Ascaris lubnicoides, Ascaris* spp., *Brugia malayi, Brugia timoni, Bunostomum* spp., *Chabertia* spp., *Clononchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebonni, Strongyloides stercoralis, Stronyloides* spp., *Taenia saginata, Taenia solium, Trichinella spinalis, Trichinella nativa, Trichinella britovi, Trichinella nelsoni, Trichinella pseudopsinalis, Tnichostrongulus* spp., *Trichuris trichuria, Wuchereria bancrofti;*
(17) from the order of Heteroptera, for example, *Anasa tristis, Antestiopsis* spp., *Blissus* spp., *Caloconis* spp., *Campylomma livida, Cavelenius* spp., *Cimex* spp., *Creontiades dilutus, Dasynus pipenis, Dichelops funcatus, Diconocoris hewetti, Dysdercus* spp., *Euschistus* spp., *Eurygaster* spp., *Heliopeltis* spp., *Honcias nobilellus, Leptoconisa* spp., *Leptoglossus phyllopus, Lygus* spp., *Macropes excavatus, Mimidae, Nezara* spp., *Oebalus* spp., *Pentomidae, Piesma quadrata, Piezodorus* spp., *Psallus seniatus, Pseudacysta persea, Rhodnius* spp., *Sahlbergella singulanis, Scotinophora* spp., *Stephanitis nashi, Tibraca* spp., *Triatoma* spp.;
(18) from the order of Homoptera, for example, *Acynthosiphon* spp., *Aeneolamia* spp., *Agonoscena* spp., *Aleunodes* spp., *Aleunolobus banodensis, Aleunothnixus* spp., *Amnasca* spp., *Anunaphis candui, Aonidiella* spp., *Aphanostigma pini, Aphis* spp., *Anbonidia apicalis, Aspidiella* spp., *Aspidiotus* spp., *Atanus* spp., *Aulaconthum solani, Bemisia* spp., *Brachycaudus helichrysii, Brachycolus* spp., *Breviconyne brassicae, Calligypona manginata, Carneocephala fulgida, Cenatovacuna lanigena, Cencopidae, Cenoplastes* spp., *Chaetosiphon fragaefolii, Chionaspis tegalensis, Chlonita onukii, Chromaphis juglandicola, Chrysomphalus ficus, Cicadulina mbila, Coccomytilus halli, Coccus* spp., *Cryptomyzus nibis, Dalbulus* spp., *Dialeunodes* spp., *Diaphonina* spp., *Diaspis* spp., *Dorsalis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*
(19) from the order of Isoptera, for example, *Reticulitermes* spp., *Odontotermes* spp.;
(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mods repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the invention, the compounds and compositions of the invention can be applied against a single pest or combinations thereof.

The above description of the invention is intended to be illustrative and not limiting. Various changes or modifications in the embodiments described may occur to those skilled in the art. These can be made without departing from the scope or spirit of the invention.

The invention is further described, for example, in the following non-limiting examples. Better understanding of the present invention and of its many advantages will be had from the following non-limiting examples, given by way of illustration. It will be apparent to those skilled in the art that these examples are non-limiting, and that similar methods to achieve the following transformations are possible.

The following examples describe the preparation of various

Example 1

Production and Analysis of Moxidectin Crystalline Forms

Methods.

Differential Scanning Calorimetry (DSC).

The samples were subjected to three modes of testing with TA Instruments' Q100 to determine the thermal possibilities.

1. The Conventional DSC method was used involving the following steps:
   a) Equilibrate at 20° C. for 3 minutes.
   b) Ramp 10° C./minute to 250° C. [HEAT]

2. The Modulated DSC with the following sequence of steps:
   a) Equilibrate at 200° C.
   b) Modulate±1° C. every 60 seconds.
   c) Isothermal for 5 minutes.
   d) Ramp 50° C. per minute to 200° C.

3. The Heat-Cool-Heat method at a higher temperature range:
   a) Equilibrate at 20° C. for 3 minutes.
   b) Ramp 10° C./minute to 200° C. [HEAT]
   c) Ramp 10° C./minute to 20° C. [COOL]
   d) Ramp 10° C./minute to 250° C. [HEAT]

Thermal Gravity Analysis (TGA).

TGA was performed on Perkin Elmer Pyris 1 TGA instrument. Samples were equilibrated at 22° C. for 1 minute, then heat was applied at ramp of 10° C./minute to 300° C.

X-Ray Powder Diffraction (XRPD).

Patterns were obtained at room temperature on Shimadzu's XRD-6000. The isothermal measurement conditions were as follows:
Target: Cu
Voltage: 40 kV
Current: 40 mA
Divergence Slit: 1.0 mm
Anti-scatter Slit: 1.0 mm
Receiving Slit: 0.15 mm
Monochromator: None
Detector Slit: 0.15 mm
Scan range: 2 to 40 deg
Scanning Speed: 1 deg/minute
Step Size: 0.02 deg
Preset Time: 1.20 sec The XRPD diffractograms of the samples were compared with regard to peak position and relative intensity, peak shifting, and the presence or lack of peaks in certain angular regions.

Optical Microscopy.

The optical photomicrographs were obtained at room temperature on Axioskop 40 polarized light microscope from Zeiss. Under reflected light and grazing illumination, the images at 5× magnification were captured through a charge-coupled device (CCD) camera, and were processed and enhanced using Axiovision Version 4.3 software.

Attenuated Total Reflectance Infrared (ATR-IR) Spectroscopy.

A diamond ATR (Smart Orbit) accessory, and a Nicolet 6700 FTIR from ThermoFisher were used with the following instrument conditions: 1) Scan range: 4000 to 650 $cm^{-1}$; 2) 32 scans; and 3) 4 $cm^{-1}$ resolution.

Raman Spectroscopy.

DXR Raman Microscope from ThermoFisher was used with the following instrument conditions: 1) Exposure time=20s; 2) 32 scans; 3) 24 sample scans; and 4) 32 background scans.

Moisture Sorption Gravimetric Analysis (SGA).

Utilizing a dynamic SGA100 from VTI, adsorption and desorption profiles were obtained with the following conditions: 1) Isothermal @ 25° C.; 2) Maximum Equilibration Time of 10 minutes; 3) 0.0010 wt % in 5 minutes; and 4) % RH (Relative Humidity) Steps of 5 to 95, and 95 to 5 @ 5% increments.

Thermal Analysis of Commercial Moxidectin (Lot #S090601)

Figure 3:
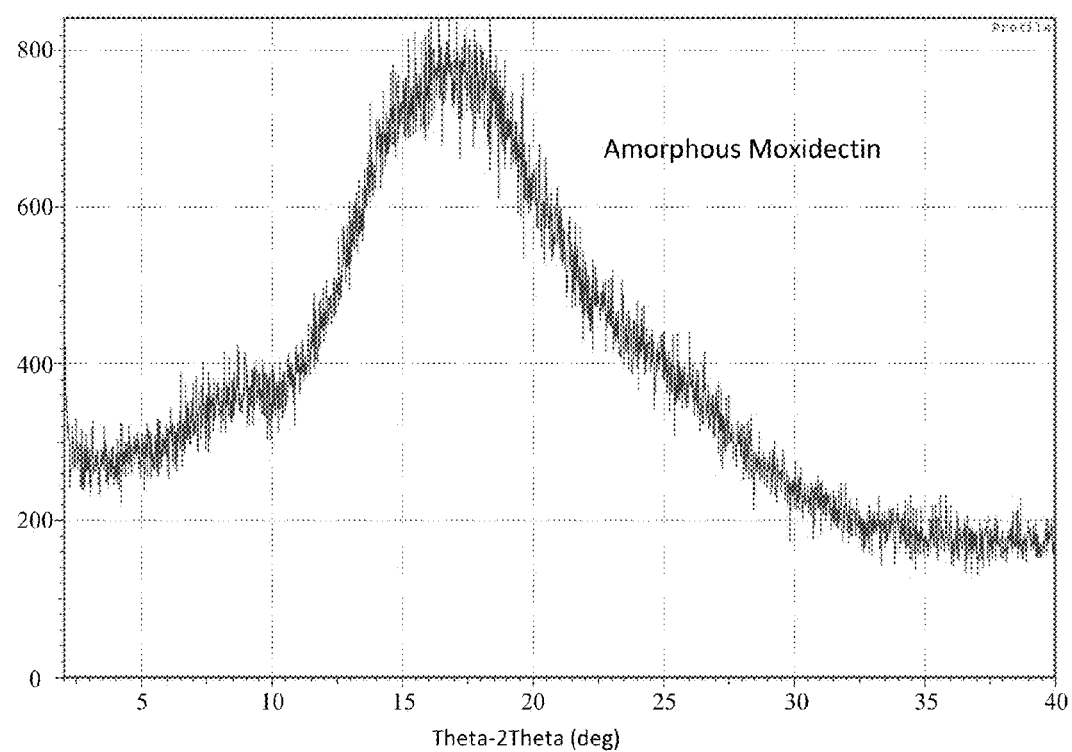
FIG. 3 depicts a PRXD of moxidectin (lot S090601, amorphous form)

The conventional DSC of lot S090601 is depicted in FIG. 2A. It shows an endothermal event at 114° C., which is attributed to the glass transition of moxidectin. Starting from 174° C., it presents a broad exotherm centered at 186° C., which is presumably the crystallization of rubbery moxidectin. Immediately following the crystallization, a sharp endotherm occurs at 206° C., which demonstrates the melting point of crystalline moxidectin Form A. The moxidectin starts to decompose above 230° C. The PXRD confirms that the original moxidectin (lot S090601) is amorphous as shown in FIG. 3.

Figure 4:
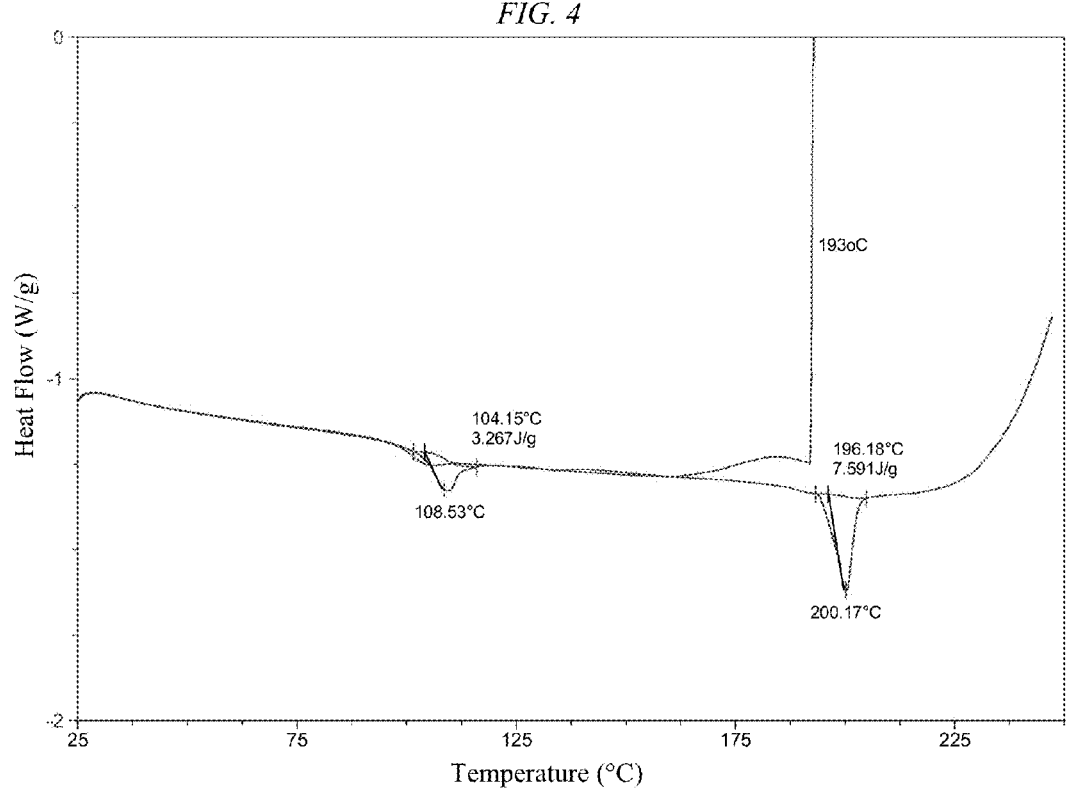
FIG. 4 depicts a heating-cooling-heating (20-193-20-250° C.) DSC cycle of moxidectin (lot S090601)
Figure 5:
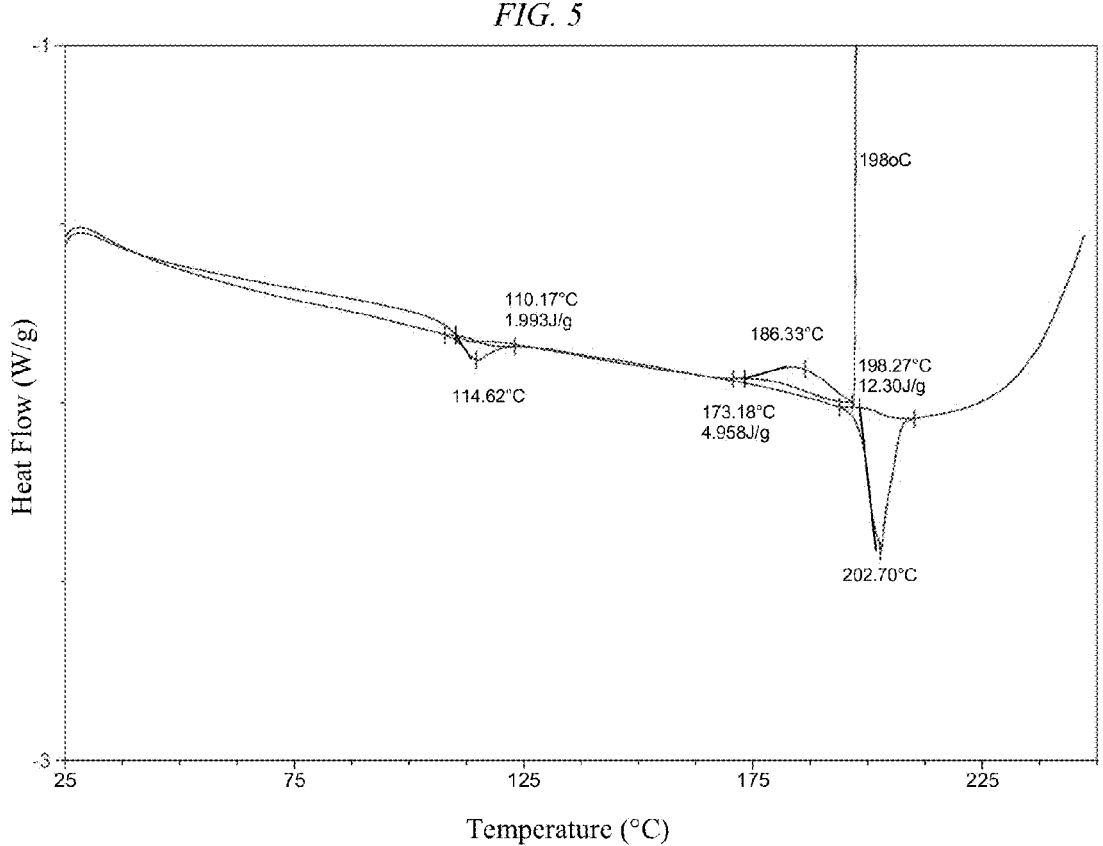
FIG. 5 depicts a heating-cooling-heating (20-198-20-250° C.) DSC cycle of moxidectin (lot S090601)
Figure 6:
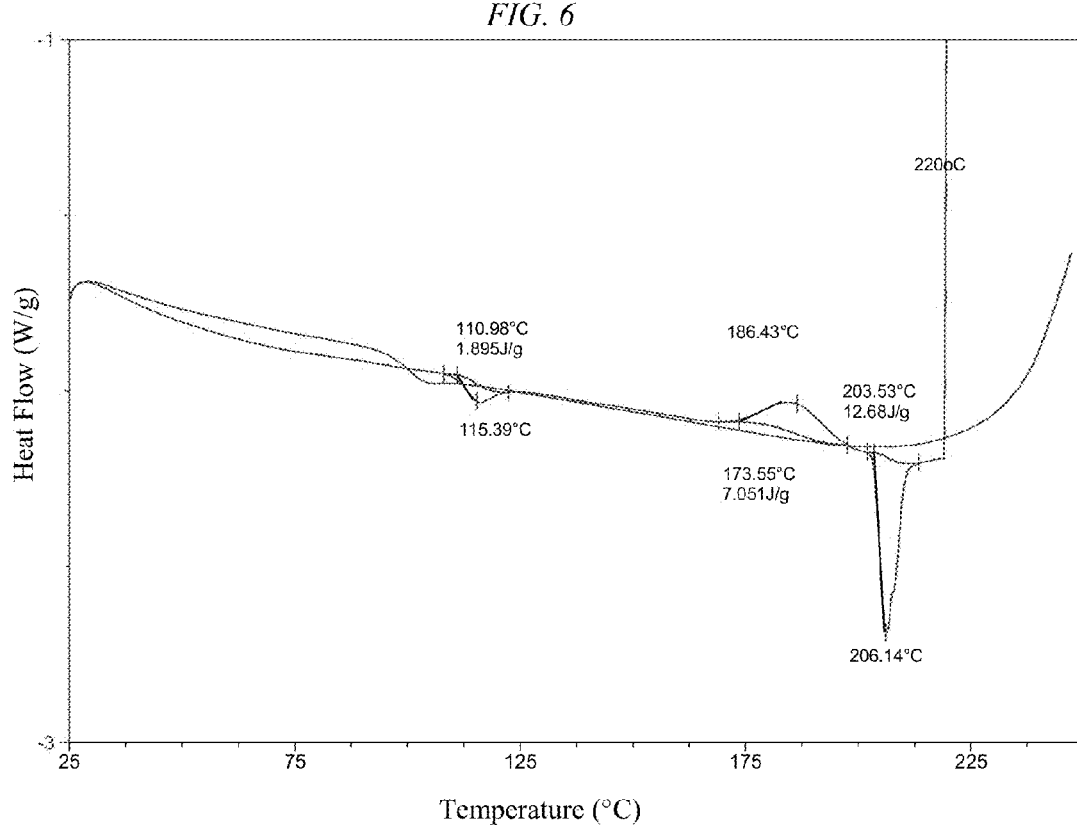
FIG. 6 depicts a heating-cooling-heating (20-220-20-250° C.) DSC cycle of moxidectin (lot S090601)

To better understand its thermal behavior, several heating-cooling-heating cycle experiments were performed. In the first experiment, the moxidectin was cooled down from 193° C., which was just above the crystallization temperature, as shown in FIG. 4. The reheating experiment showed that the sample still contained a certain amount of amorphous material due to the presence of the glass transition at 105° C. In contrast, the second heat cycle exhibited a melting endotherm without evidence of crystallization. This indicates that the moxidectin crystallization was complete during the initial heat cycle. After cooling the sample from 198° C. to a temperature below the previously observed crystallization temperature, (FIG. 5), reheating showed no evidence of the previously observed glass transition, suggesting that all of the moxidectin crystallized during the first heat cycle. This is further supported by the observation of the melting point even though no crystallization transition was observed during the second heat cycle. After cooling the sample from 220° C. (FIG. 6), which was higher than the melting point but below the decomposition temperature, the second heat cycle showed only the glass transition, indicating that the sample became amorphous upon cooling of the molten material.

Figure 7:
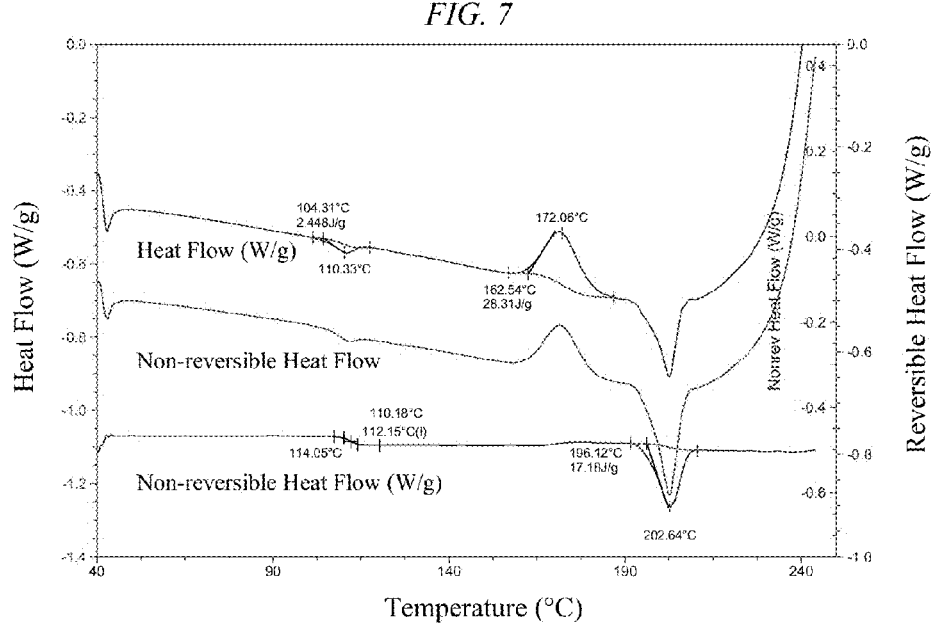
FIG. 7 depicts a MDSC curve of moxidectin (lot S090601)

The modulated DSC is shown in FIG. 7. This result is consistent with those obtained from conventional DSC. A glass transition appeared in the reversible heat flow experiment, while the relaxation enthalpy, crystallization and decomposition were observed under irreversible heat flow conditions. Melting occurred in both the reversible and irreversible heat flow modes.

Thermally Transformed Moxidectin.

Figure 8:
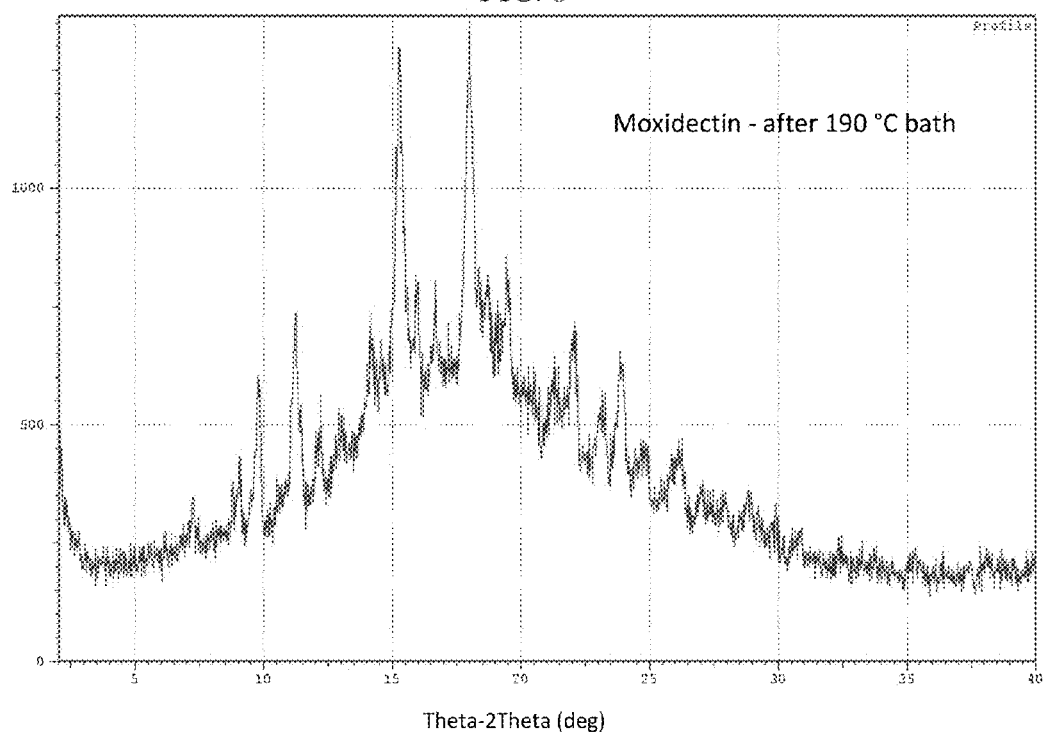
FIG. 8 depicts an X-Ray Powder Diffraction pattern (PXRD) of moxidectin (now Form A) after heating at 190° C. (lot S090601)

Approximately 1 g of moxidectin (lot S090601) was placed in a glass vial, which was then placed in a hot oil bath at ~190° C. and held at that temperature for approximately 5 minutes. Upon cooling the material had yellowed slightly. The yellowish solid was collected and ground in a mortar and pestle. To evaluate the purity of the moxidectin which had been subjected to these conditions, HPLC and LC-MS were performed. The powder was analyzed by powder x-ray diffraction (PXRD) spectroscopy. The PXRD pattern shows significant diffraction peaks indicative of the presence of a sizable amount of crystalline material although a certain amount of amorphous material still remained as evidenced by the halo envelope in the diffraction pattern. This indicates that amorphous moxidectin crystallizes upon heating to 190° C. (FIG. 8).

Figure 9:
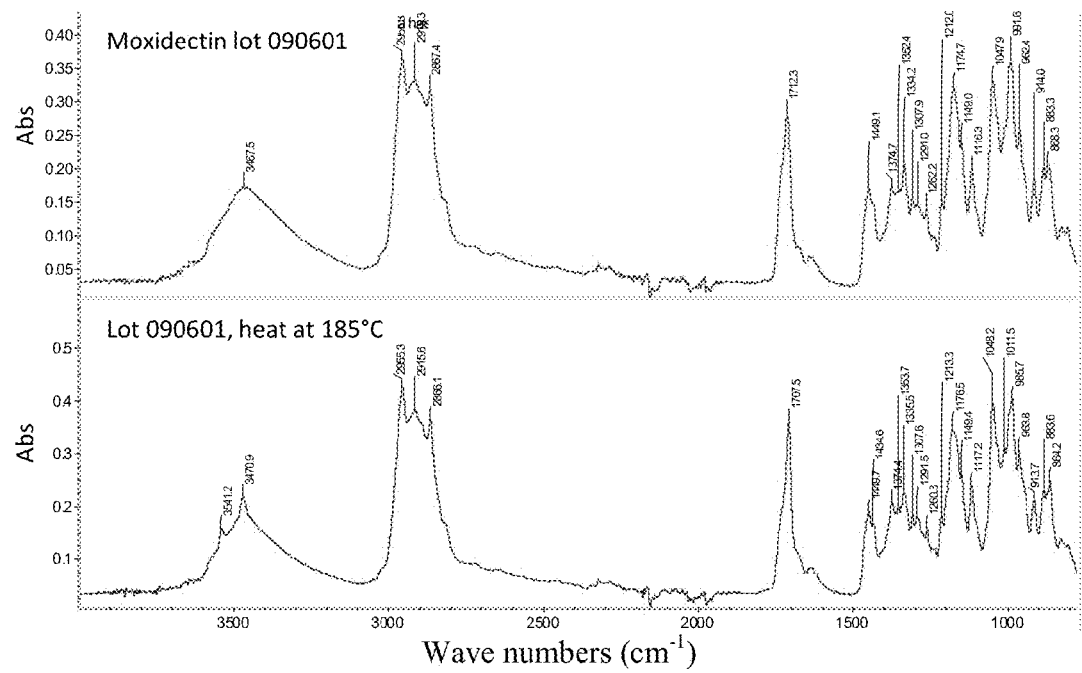
FIG. 9 depicts the IR spectra of moxidectin (top: amorphous moxidectin, lot 5090601; bottom: thermally transformed crystalline moxidectin, Form A)
Figure 10:
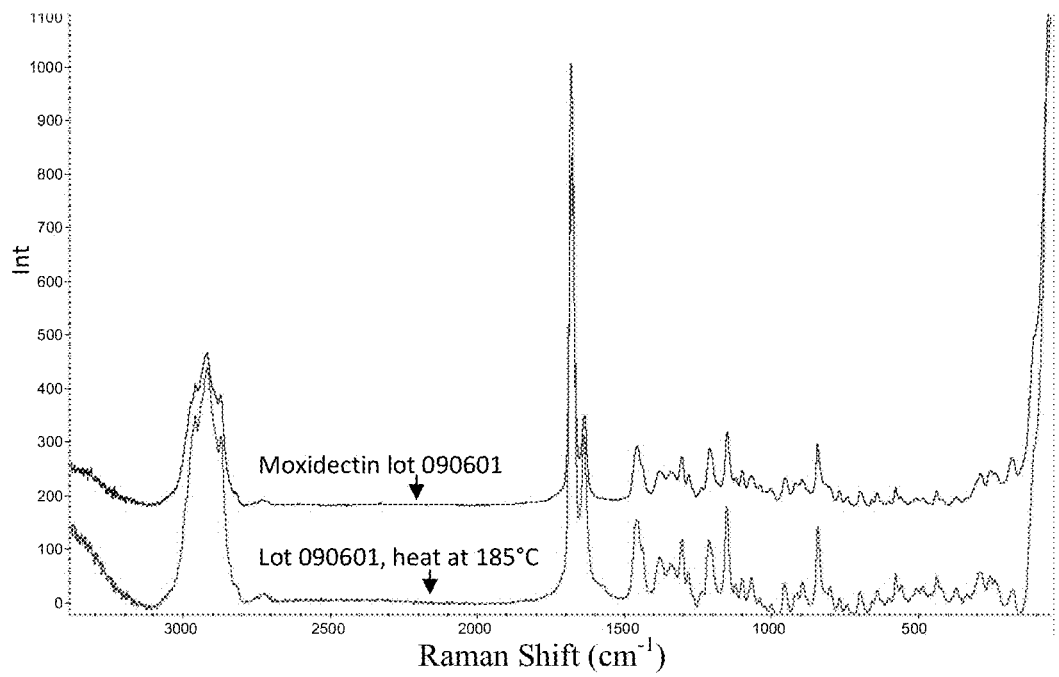
FIG. 10 depicts the Raman spectra for moxidectin (black: amorphous moxidectin, lot S090601; grey: thermally transformed crystalline moxidectin);

The IR and Raman spectra of amorphous and thermally transformed crystalline moxidectin are shown in FIG. 9 and FIG. 10. Compared with amorphous moxidectin, crystalline moxidectin shows two sharp peaks, 3471 $cm^{-1}$ and 3541 $cm^{-1}$ superimposed on the broad peak around 3500 $cm^{-1}$. The carbonyl stretching vibration of crystalline moxidectin shows slight red shift to 1707 $cm^{-1}$ from 1712 $cm^{-1}$. This demonstrates that these peaks in the IR can be used to distinguish this crystalline form from amorphous moxidectin.

A hot stage microscopic image was taken (FIG. 11) of this thermal transition. The bulk, amorphous moxidectin demonstrated a wetting phenomenon around 120° C. The wetting increased significantly with increasing temperature and the sample appeared to flow, indicating that the sample had undergone a glass transition. This parallels the DSC observation. Between 120 and 170° C., the sample maintained this rubbery state. At about 185° C., white spots began appearing and a large patch of "prismatic crystals" appeared at 190° C. More crystals developed with increasing temperature to 205° C. Above 210° C., the crystals began to melt with completion at 218° C. The compound decomposed around 230° C. The hot-stage microscopic experiment verified the DSC result, confirming the transformation of moxidectin from amorphous state through glass transition to a rubbery state followed by crystallization and subsequent melting then decomposition.

Preparation and Characterization of Moxidectin/MeOH.

Figure 12:
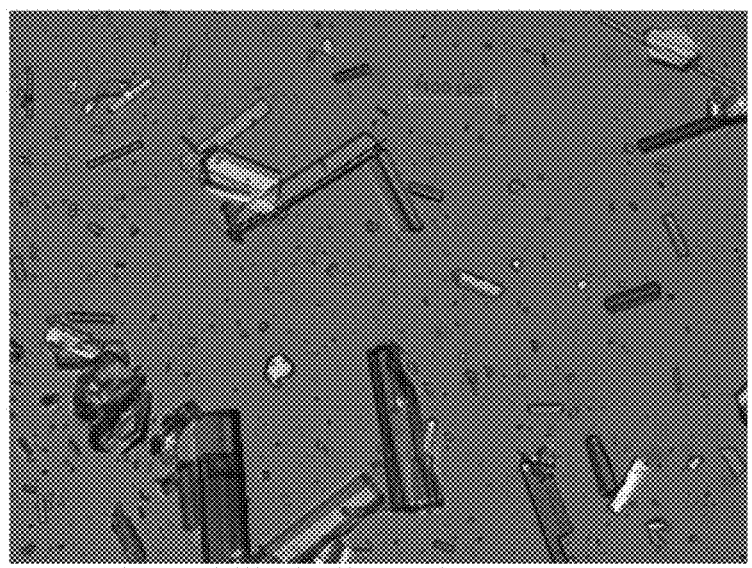
Figure 13:
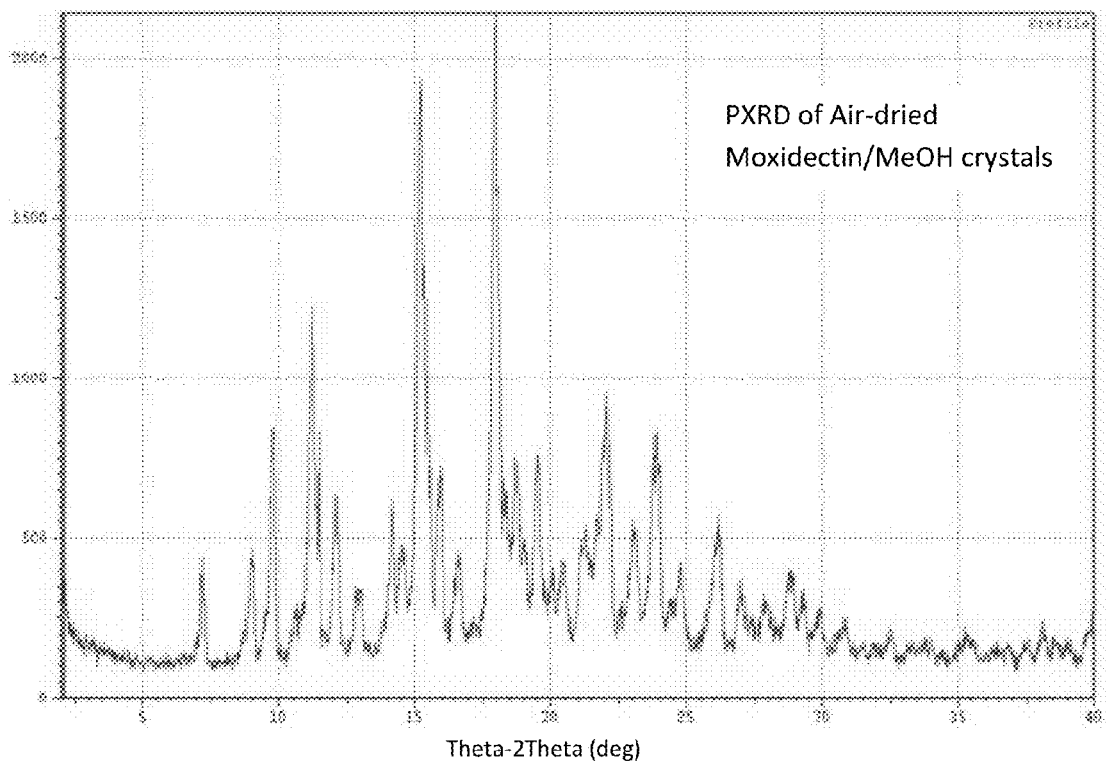

To 0.5 ml methanol at 50-60° C. amorphous moxidectin (lot#S090601) was added gradually until the solution became saturated. The resulting mixture was cooled to room temperature and rod-like crystals formed after a short period of time. The solid was filtered and the crystal image is presented in FIG. 12. The crystals were birefringent, indicative of crystallinity. Moxidectin/MeOH crystals were dried in air for 1 h. The powder X-ray diffraction confirmed its high degree of crystallinity (FIG. 13).

Figure 14:
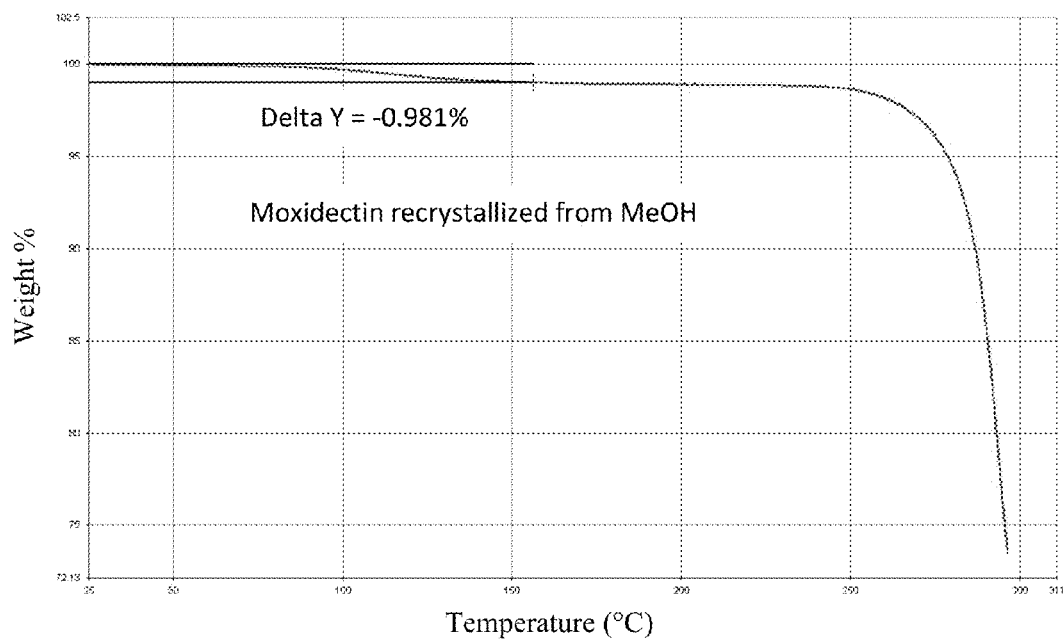

Thermal analysis of air-dried Moxdectin.MeOH crystals demonstrated a weight loss of 0.98% between 50-150° C. (FIG. 14). The compound decomposes above 250° C.

Figure 15:
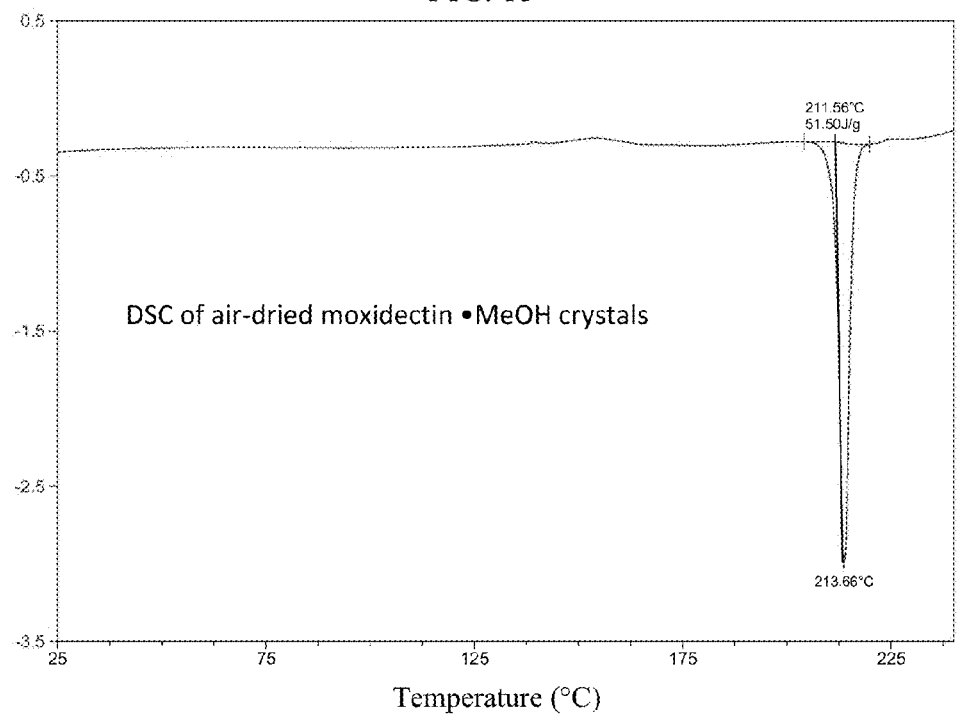

DSC did not show the corresponding solvent loss due to its low content. It exhibits a small exotherm around 150° C., then melts at 214° C. (FIG. 15). The small peak at 150° C. results from either solvent evaporation or phase transition. The melting point is very close to that obtained from amorphous moxidectin, suggesting that they might be the same form.

Preparation and characterization of Moxidectin.EtOH.

Figure 16:
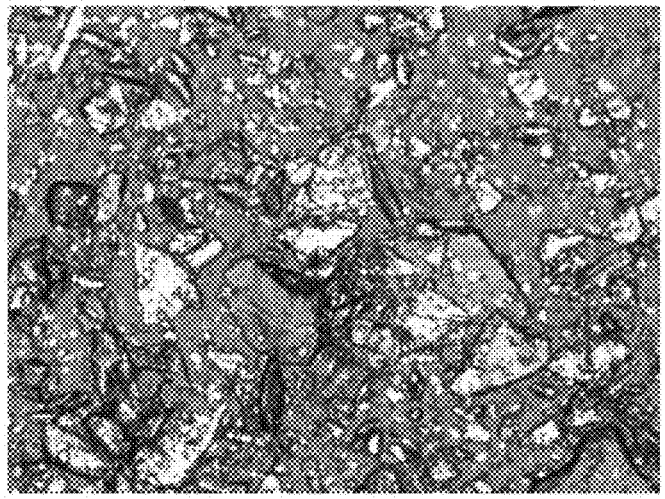

To 1 ml ethanol, amorphous moxidectin (lot#S090601) was added gradually at 50-60° C. until the solution was saturated. The resulting mixture was left at room temperature and quickly formed large crystals having approximate dimensions of about 2 mm×2 mm×0.5 mm. One representative crystal was crushed and the crystal image was taken, which is depicted in FIG. 16.

Figure 17:
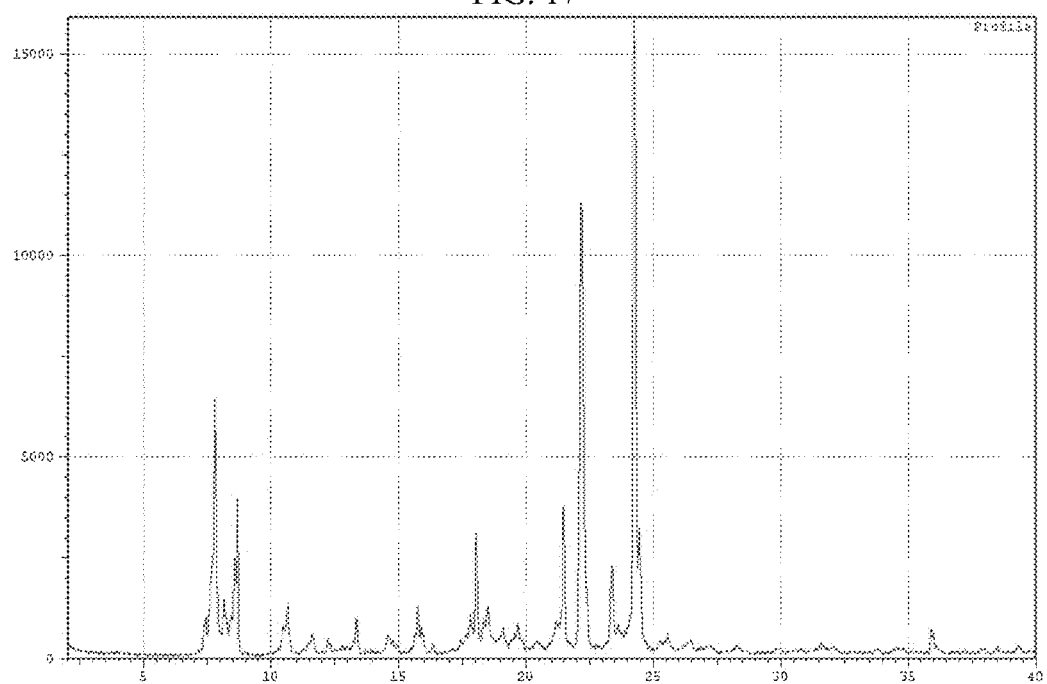

Moxidectin.EtOH crystals were separated and air-dried for 2 h. The crystals were ground with a mortar and pestle and analyzed by powder X-ray diffraction and thermal analysis. PXRD shows a strong diffraction pattern (FIG. 17), which is different from that of moxidectin MeOH, indicating that they have different crystal forms.

Figure 18:
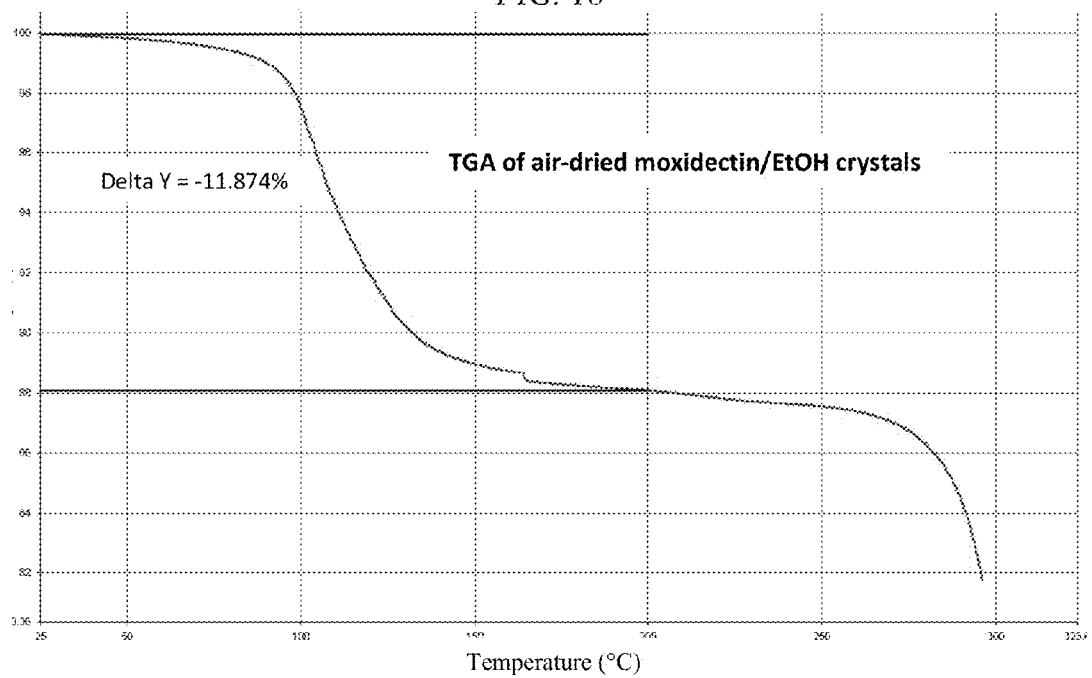

The thermal gravimetric analysis of air-dried Moxidectin.EtOH demonstrated a weight loss of 11.87% upon heating from 25 to 200° C. (FIG. 18). This weight loss roughly corresponds to two mole of ethanol per mole of moxidectin. The theoretical calculation based on moxidectin:ethanol=1:2 gives 12.57% ethanol weight content which is consistent with the experimental value. The compound decomposes above 250° C.

Figure 19:
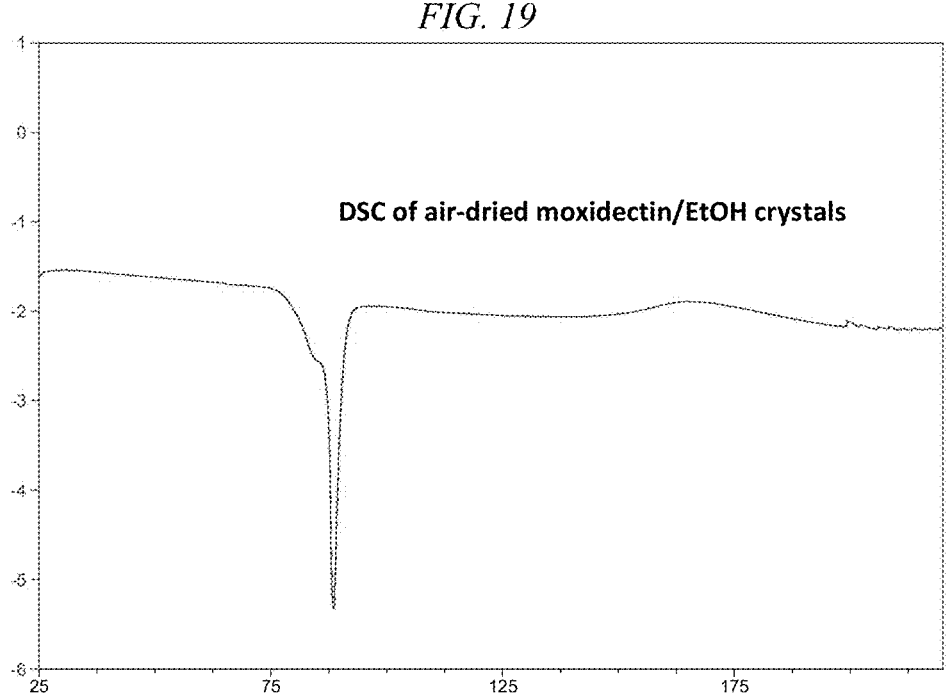

The DSC of this material exhibits a sharp endotherm with a shoulder at 90° C., which probably corresponds to loss of ethanol as shown in FIG. 19.

Figure 20:
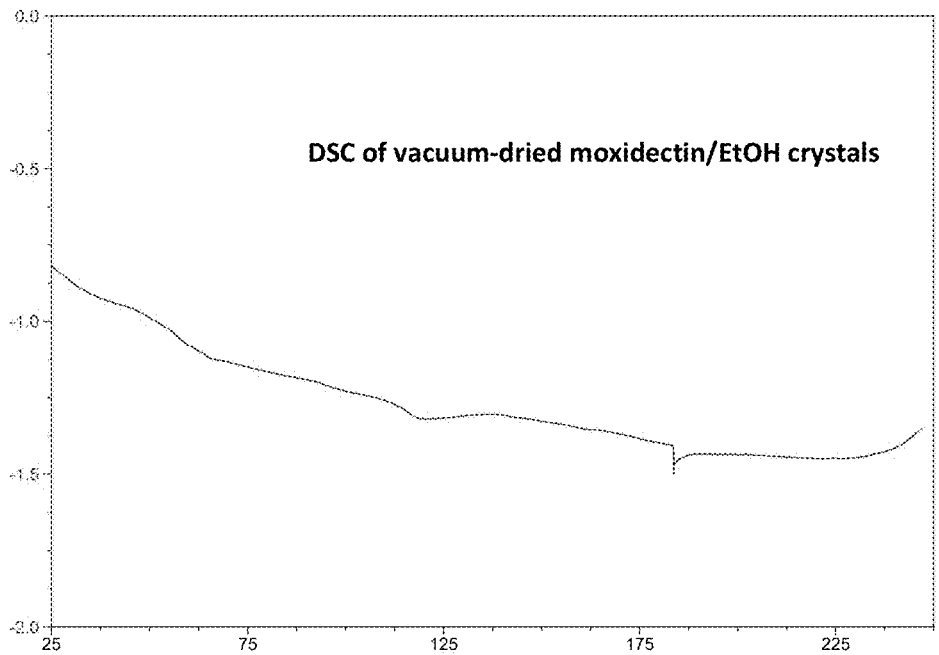
Figure 21:
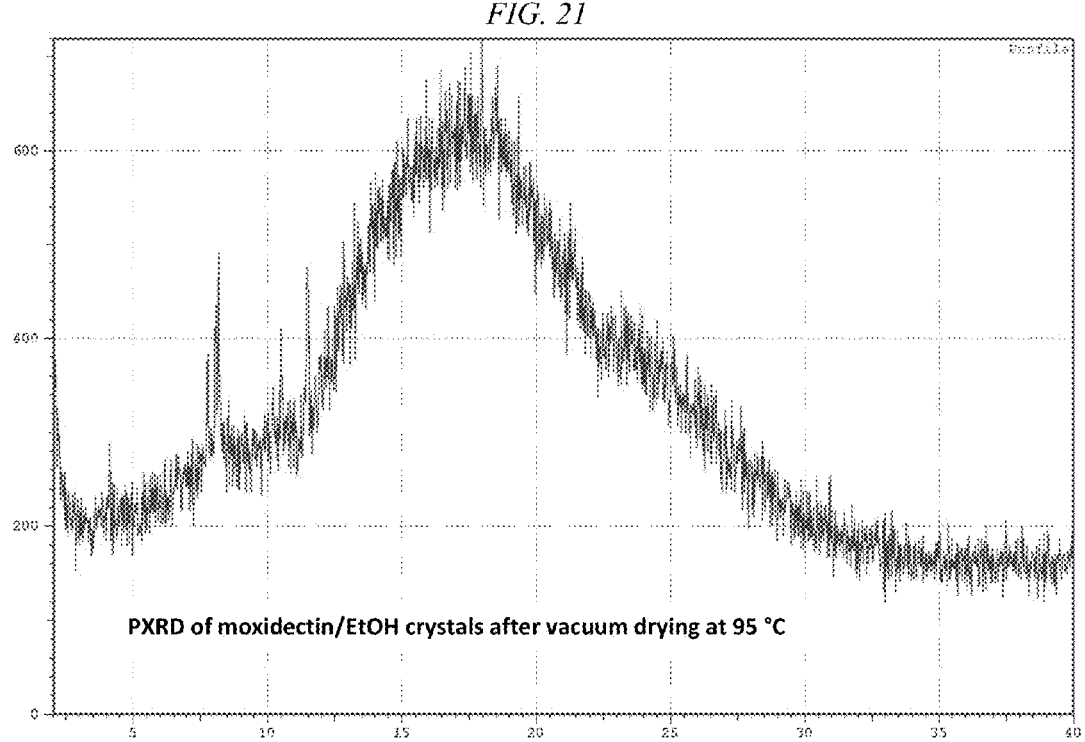

The Moxidectin.EtOH crystals were dried under vacuum at 100° C. for 4 h. DSC shows the vacuum-dried moxidectin became amorphous (FIG. 20). This is further confirmed by powder X-ray diffraction. Only a few small scattered peaks appear on the PXRD (FIG. 21), due likely to incomplete collapse of the structure upon removal of the solvent.

The single crystal structure of crystalline Moxidectin.EtOH was determined demonstrating a monoclinic $P2_1$ space group with the cell parameter a=11.2731(15) Å, b=8.9286(12) Å, c=21.955(3) Å, β=93.623(2)°, V=2205.4(5) Å$^3$, Z=2.

Figure 22:
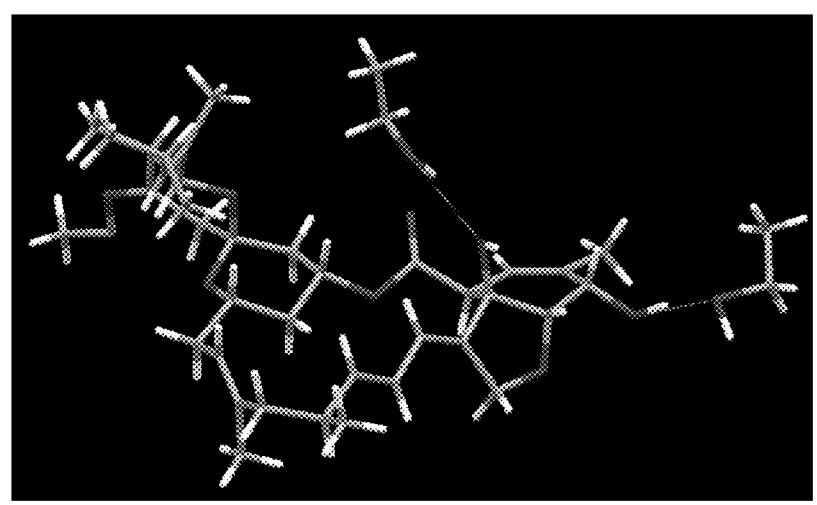
Figure 23:
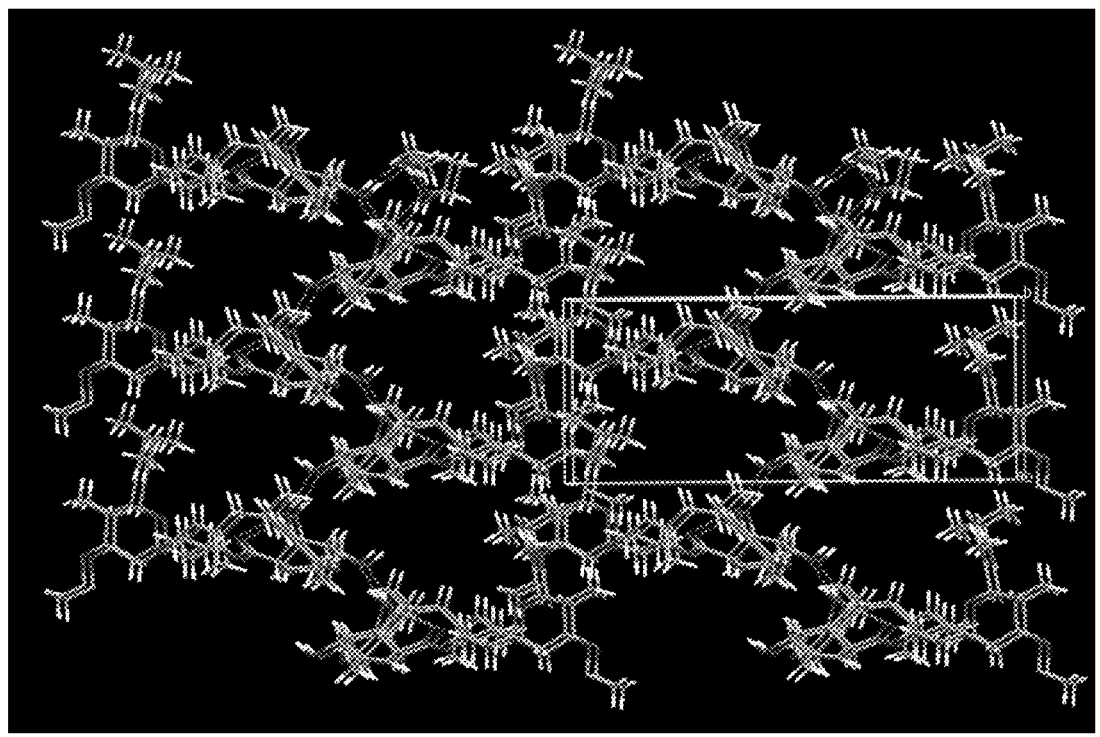

There are one moxidectin and two ethanol molecules per asymmetric unit as depicted in FIG. 22. This is consistent with the TGA result. One ethanol is hydrogen-bonded with one hydroxyl group of moxidectin as a donor and the other ethanol is hydrogen bonded to another hydroxyl group of moxidectin as an acceptor. Moxidectin molecules are connected together by hydrogen bonds, forming a channel along the crystallographic a direction, in which ethanol molecules are accommodated (FIG. 23).

Preparation and Characterization of Moxidectin.IPA.

Figure 24:
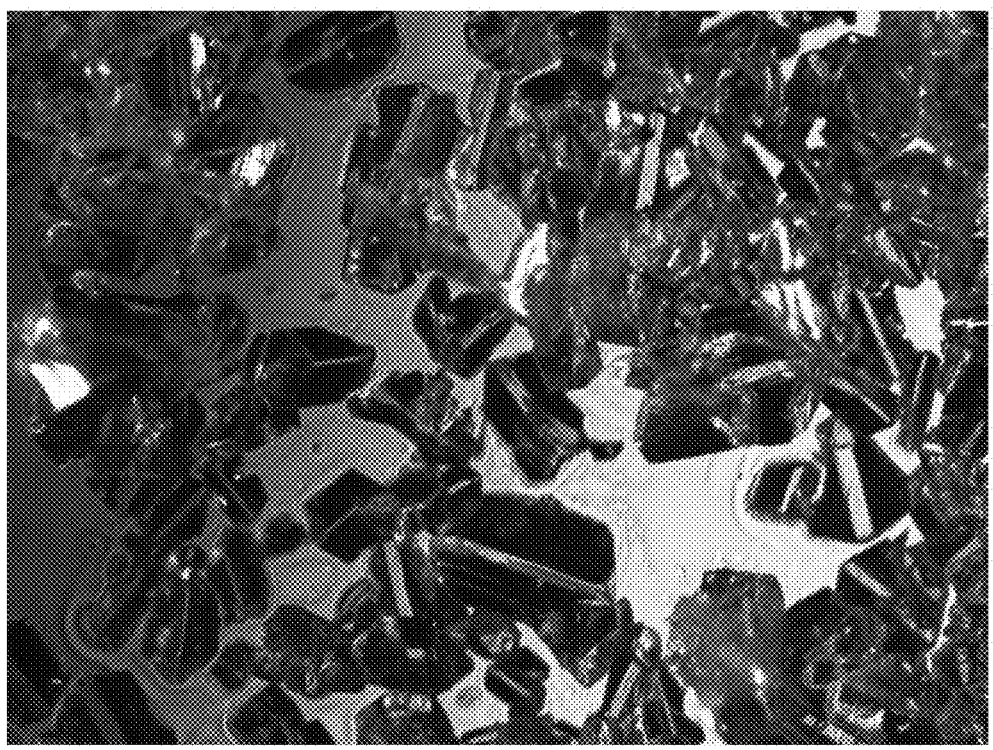
Figure 25:
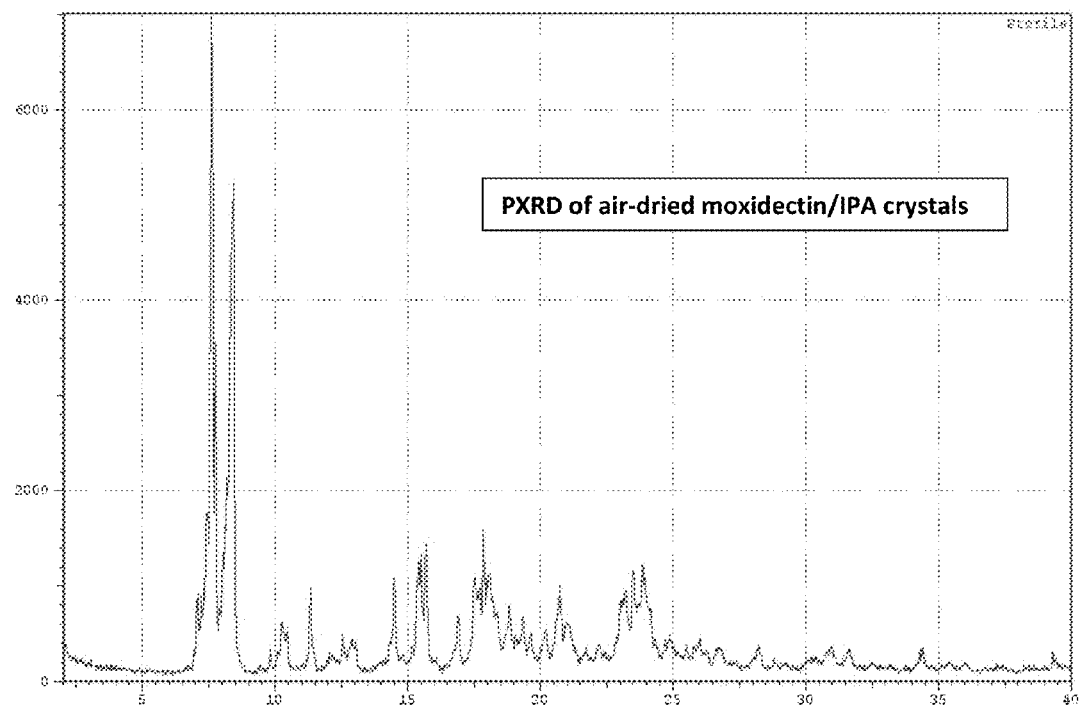
Figure 26:
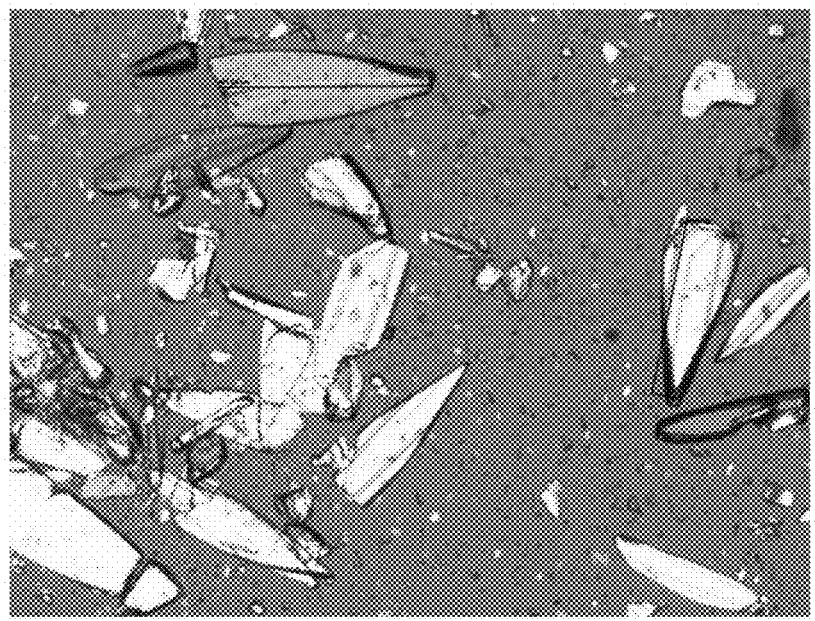
Figure 27:
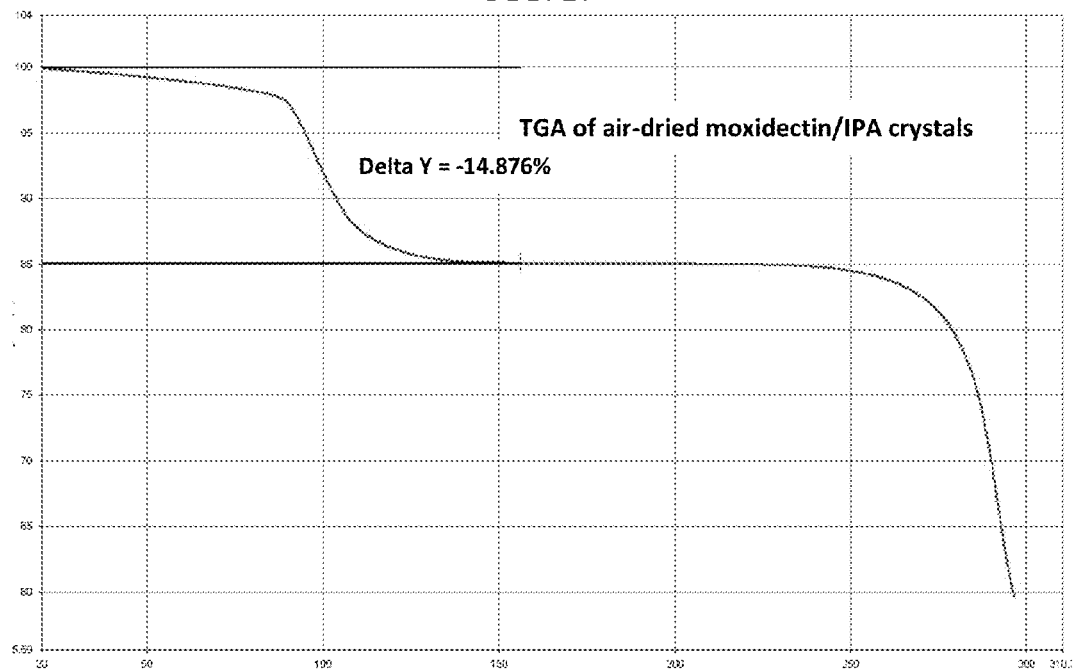

To 1 ml isopropanol solution, amorphous moxidectin (lot#S090601) was added gradually to saturation at 50-60° C. The resulting solution was cooled and held at room temperature resulting in rapid formation of large prismatic crystals. The crystal image was taken and depicted in FIG. 24. Moxidectin IPA crystals were isolated and air-dried for 2 h. Powder X-ray diffraction shows that these crystals are highly crystalline (FIG. 25). When moxidectin (lot#070201, which does not contain BHT) was used for crystallization, the crystals were also formed as shown in FIG. 26. The thermal analysis of air-dried Moxidectin IPA crystals displayed a single weight loss of 14.87% from 25-200° C. (FIG. 27). This weight loss approximately corresponds to two moles of IPA per moxidectin. The theoretical calculation based on moxidectin:IPA=1:2 gives 15.78% IPA weight content which is in reasonably good agreement with the experimental data. The compound decomposes above 250° C.

Figure 28:
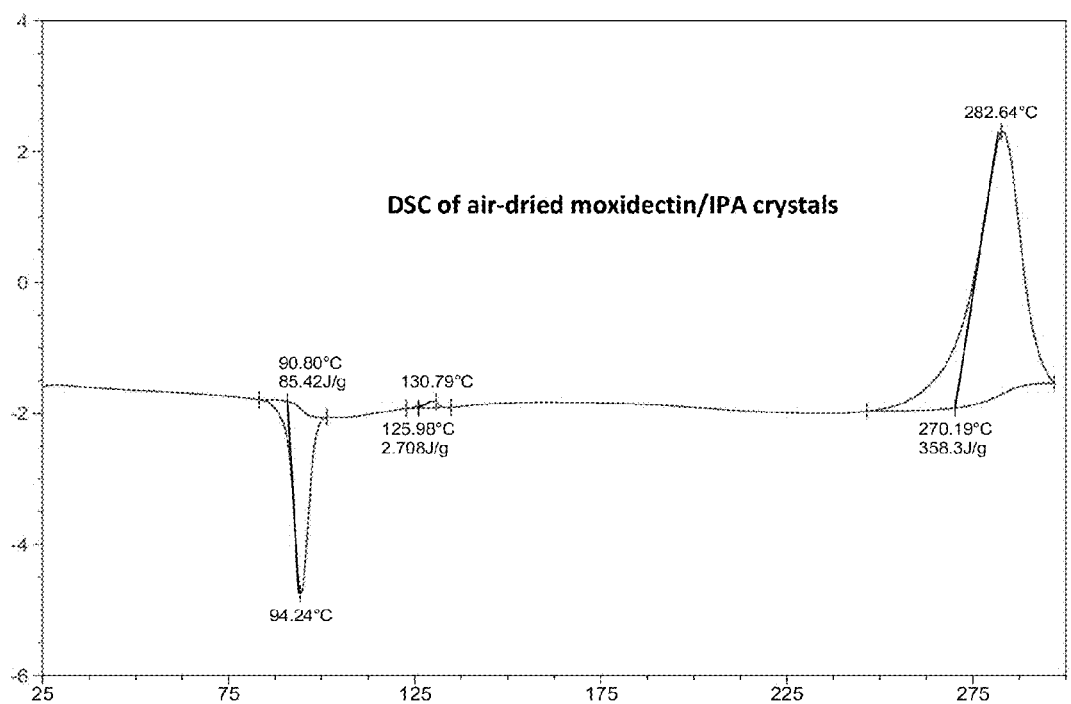

DSC of this material demonstrated a sharp endotherm with a shoulder at 90° C. (FIG. 28), which probably corresponds to the solvent loss of IPA. The small peak at 130° C. results from either solvent evaporation or phase transition, and needs to be further investigated.

Figure 29:
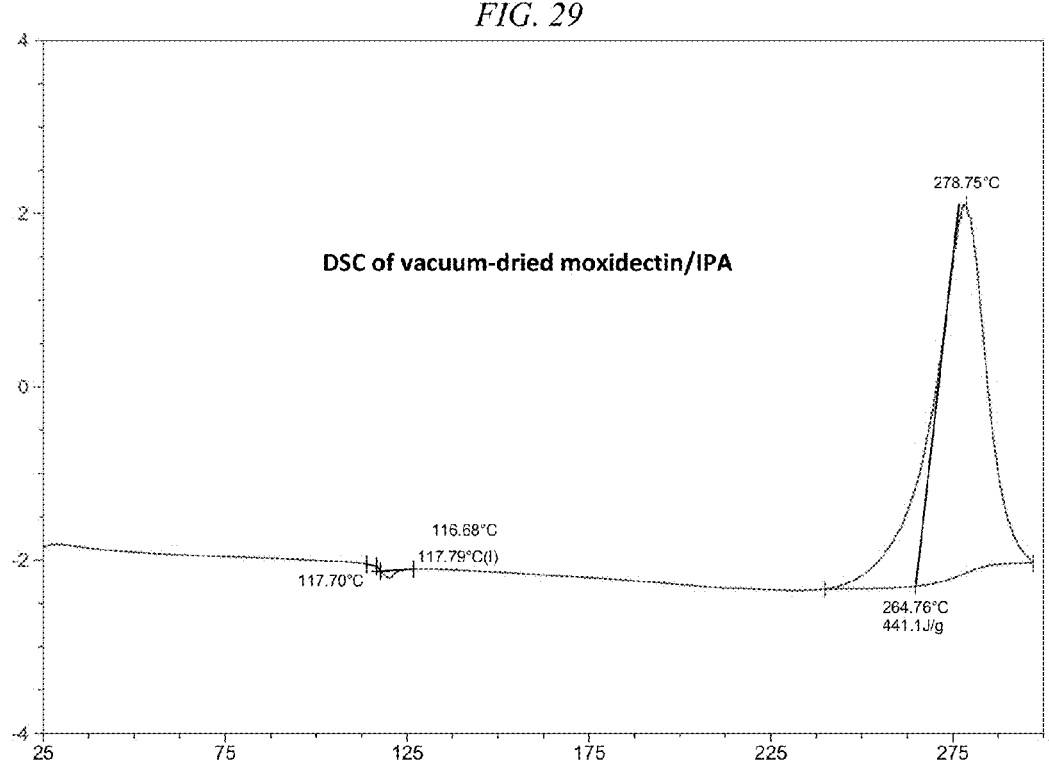

The Moxdectin IPA crystals were dried under vacuum at 100° C. for 30 min. DSC shows the vacuum-dried moxidectin becomes amorphous (FIG. 29).

Preparation and Characterization of Moxidectin n-Butanol.

Figure 30:
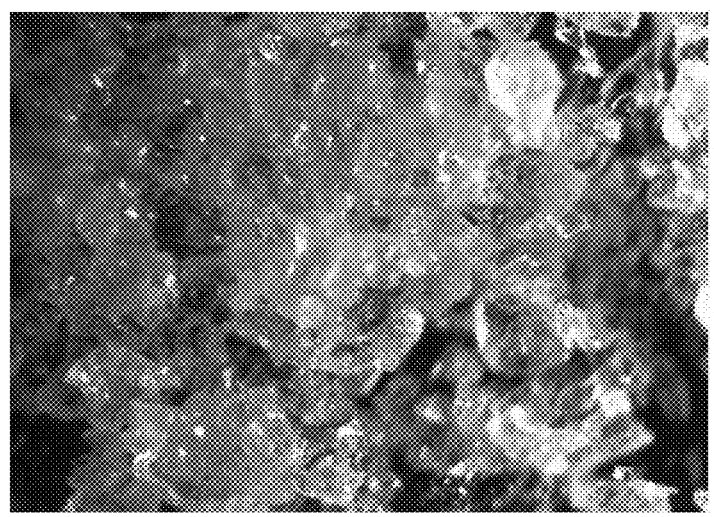
Figure 31:
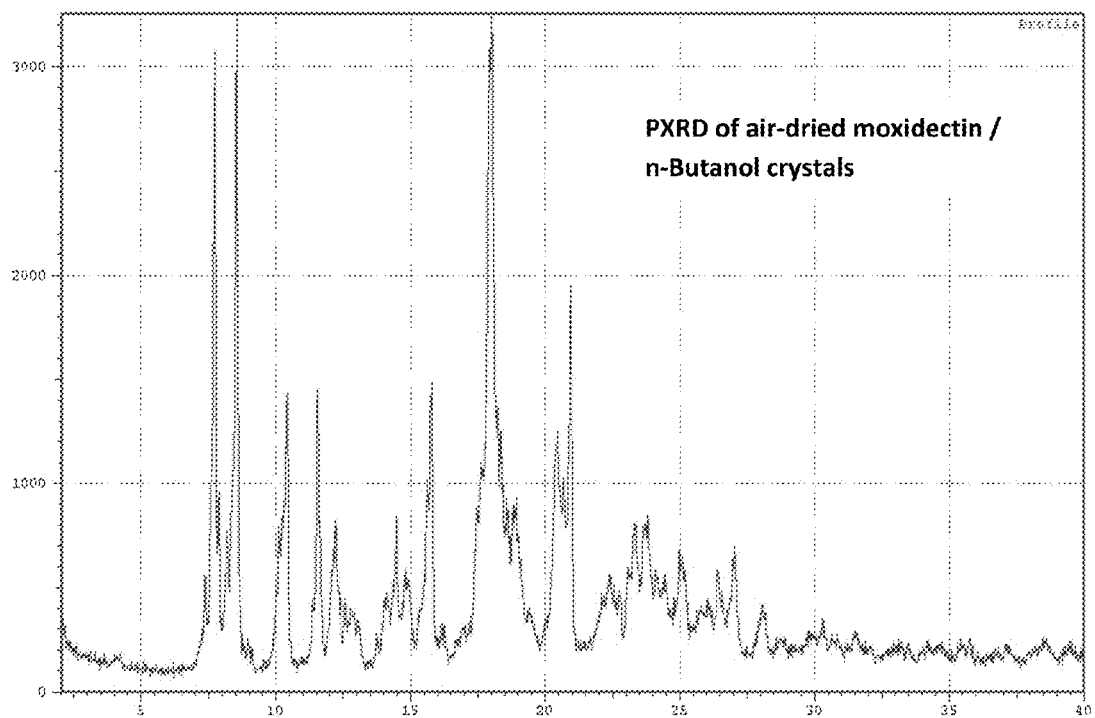

To 0.5 ml of n-butanol, amorphous moxidectin (lot#S090601) was added gradually to saturation (maintaining temperature between 50-60° C.). The mixture was then transferred to −10° C. over night, during which time crystals had formed (FIG. 30). Moxidectin/n-butanol crystals were separated and dried in air for 2 h. Powder X-ray diffraction shows that these crystals are highly crystalline (FIG. 31).

Figure 32:
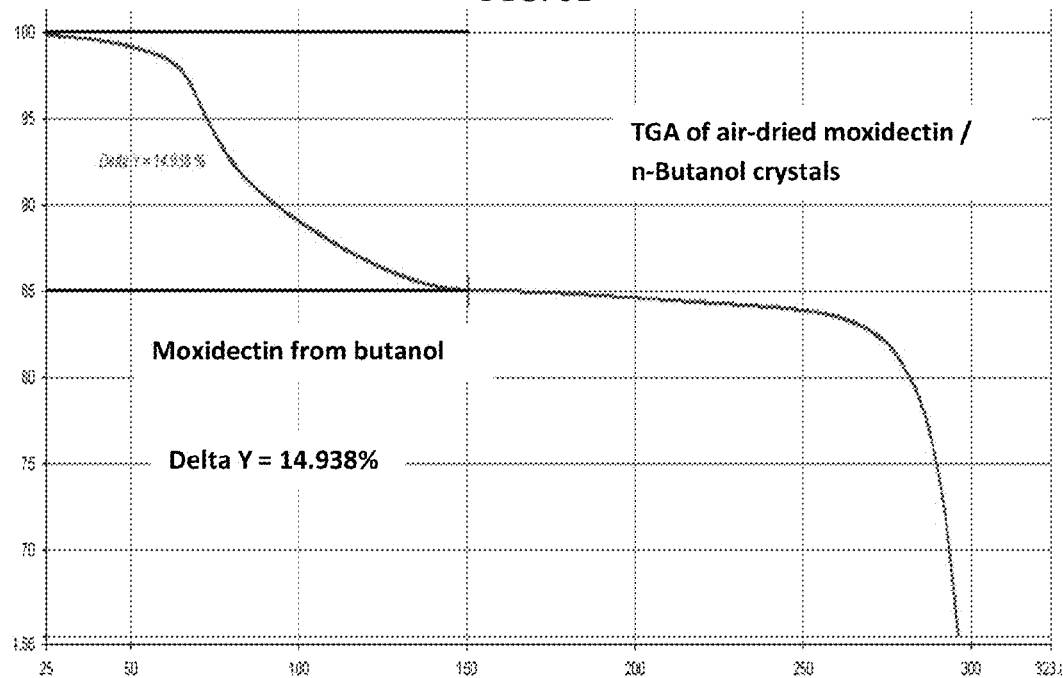

Thermal analysis of air-dried Moxidectin n-butanol displays a weight loss of 14.94% upon heating from 25 to 150° C. (FIG. 32). This weight loss corresponds to 1.5 moles of n-butanol per mole of moxidectin. The theoretical calculation based on moxidectin:n-butanol=1:1.5 gives 14.78% n-butanol weight content. The compound decomposes above 250° C.

Figure 33:
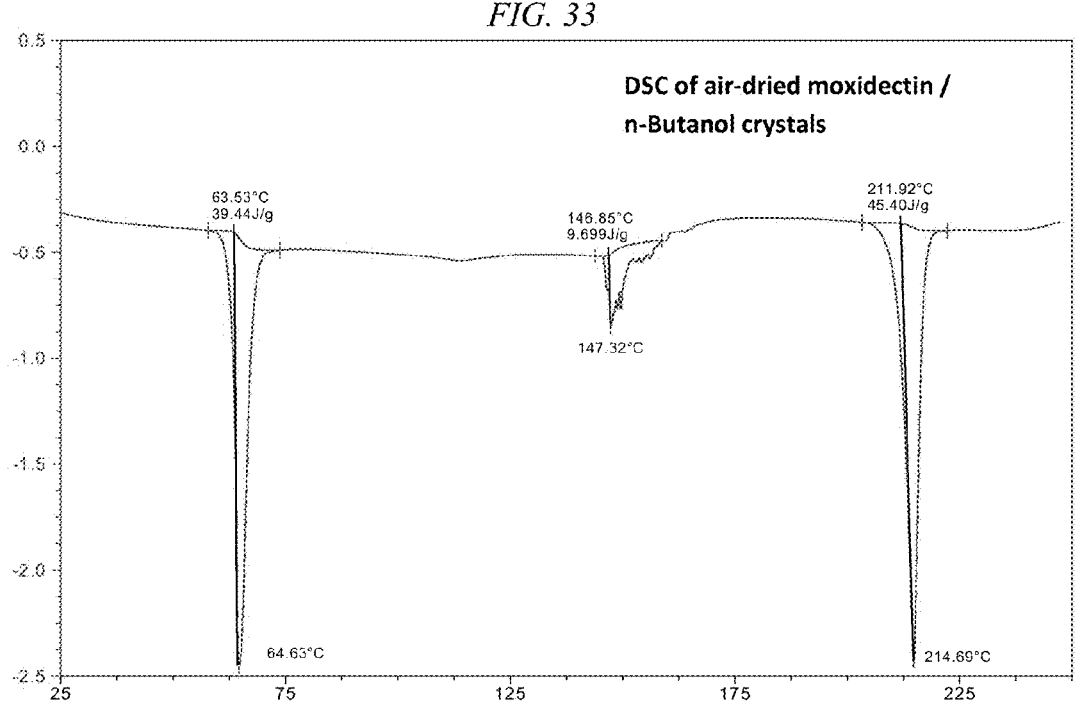

DSC exhibits a sharp endotherm at 65° C. (FIG. 33), which likely corresponds to the loss of n-butanol. The desolvated moxidectin melts at 215° C., which corresponds to the melting point of Polymorph A. The desolvation temperature is relatively low compared with moxidectin EtOH and moxidectin.IPA, suggesting that n-butanol is loosely bound with the moxidectin molecule.

Figure 34:
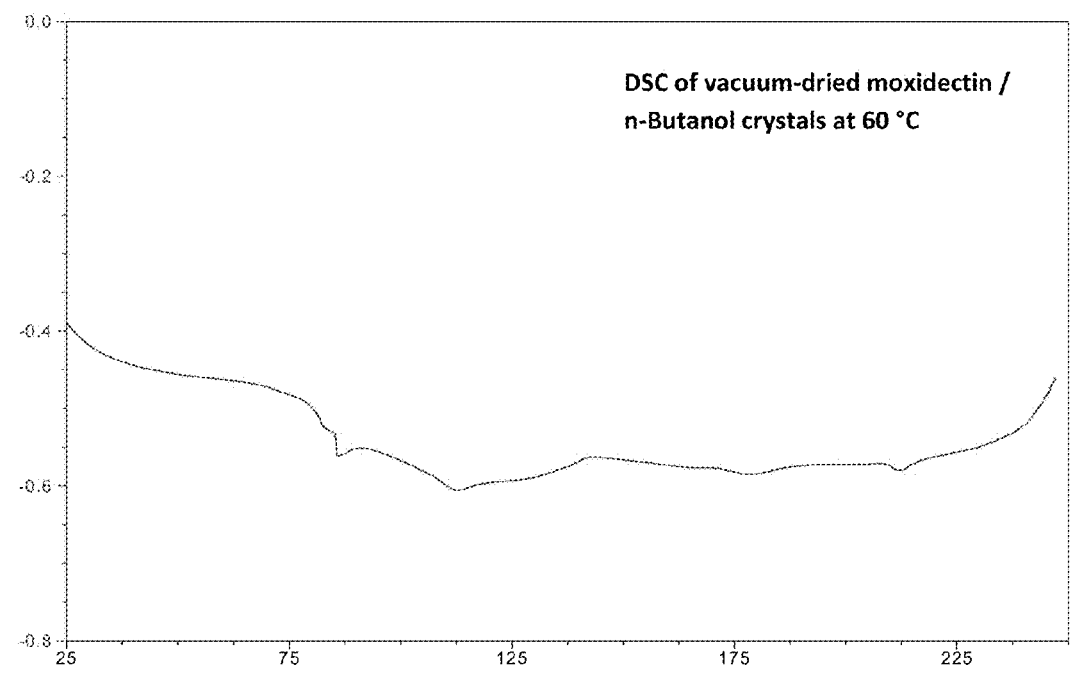
Figure 35:
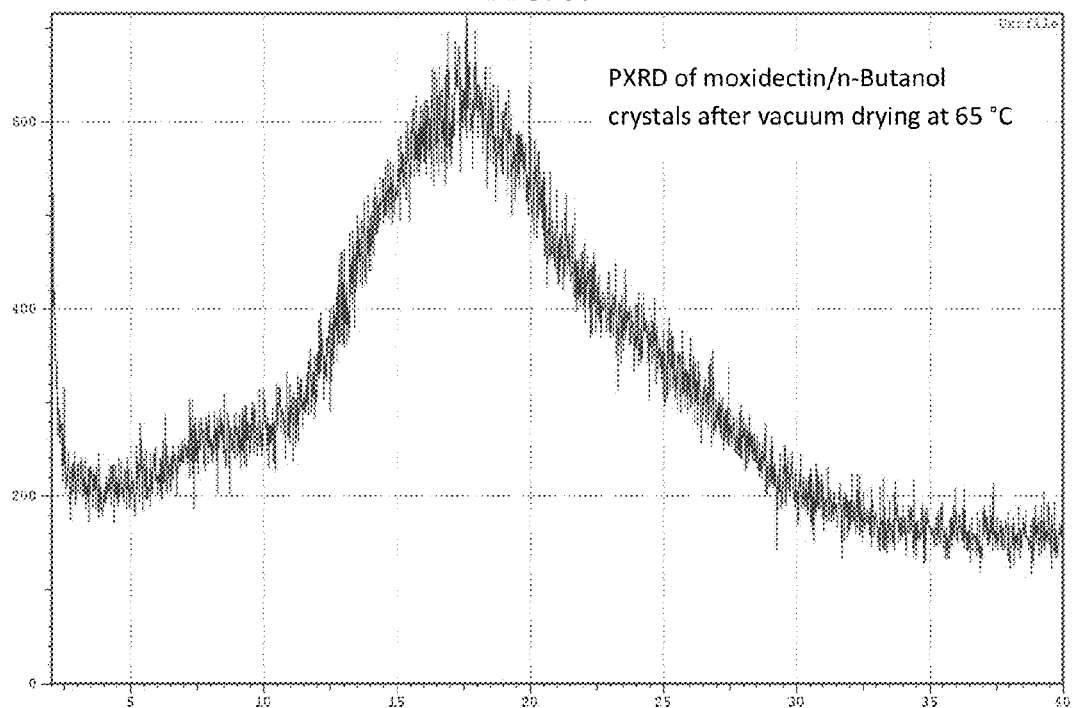
Figure 36:
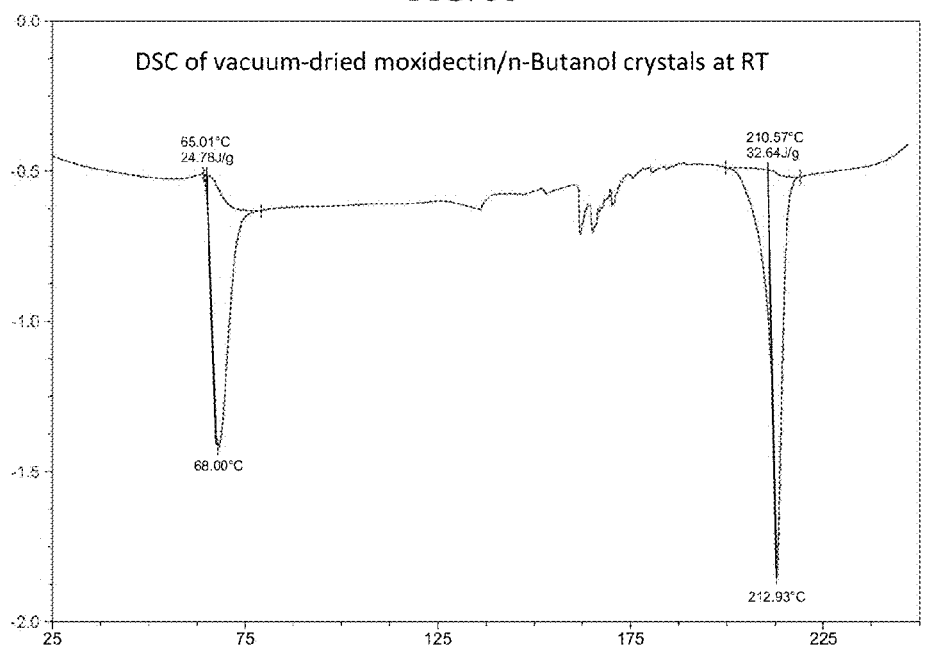

To confirm the process of desolvation of moxidectin.n-butanol, the crystals were dried under vacuum at 60° C. for 2 h. The DSC and PXRD show the vacuum-dried moxidectin became amorphous after drying (FIGS. 34 and 35). Less rigorous drying conditions did not successfully desolvate the material (FIG. 36).

Preparation and Characterization of Moxidectin MCH.

Figure 37:
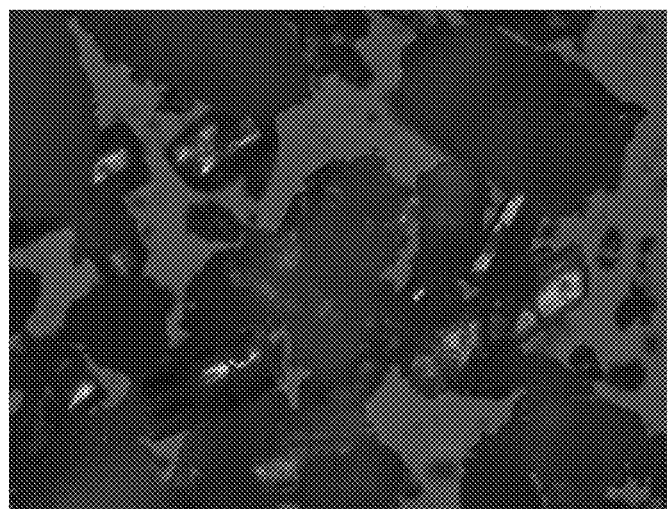
Figure 38:
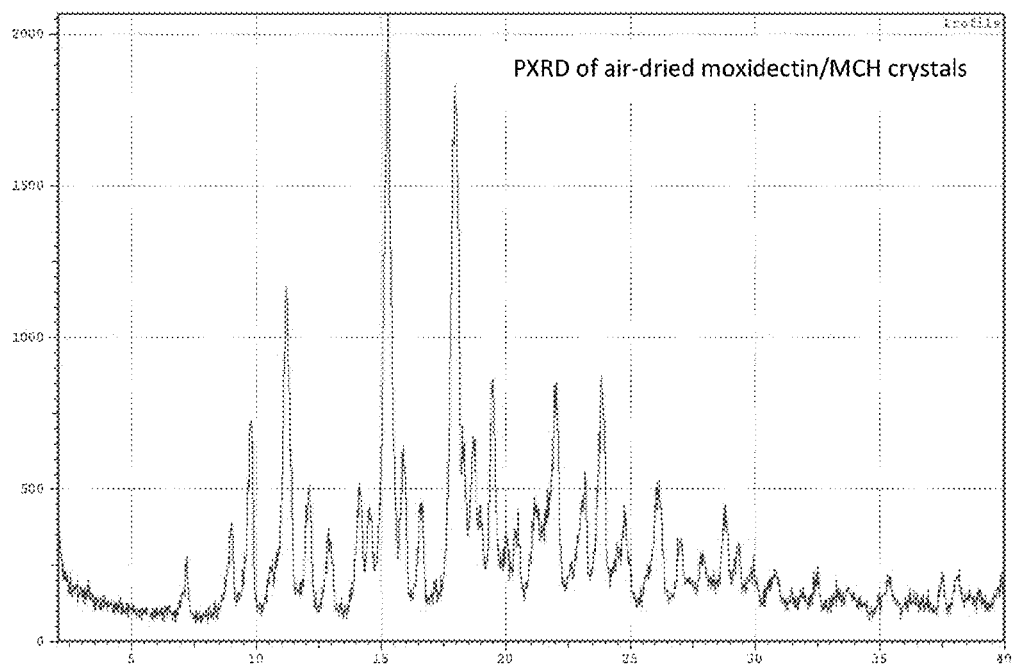

To 1 ml methylcyclohexane (MCH) solution, about 500 mg amorphous moxidectin (lot#S090601) was added while heating to 50-60° C. and the mixture was concentrated by evaporation. After cooling to room temperature, hexane was added and solid precipitate formed. The solid was washed with hexane and dried at room temperature for a short period of time (image, FIG. 37). Powder X-ray diffraction demonstrated its crystallinity (FIG. 38).

Figure 39:
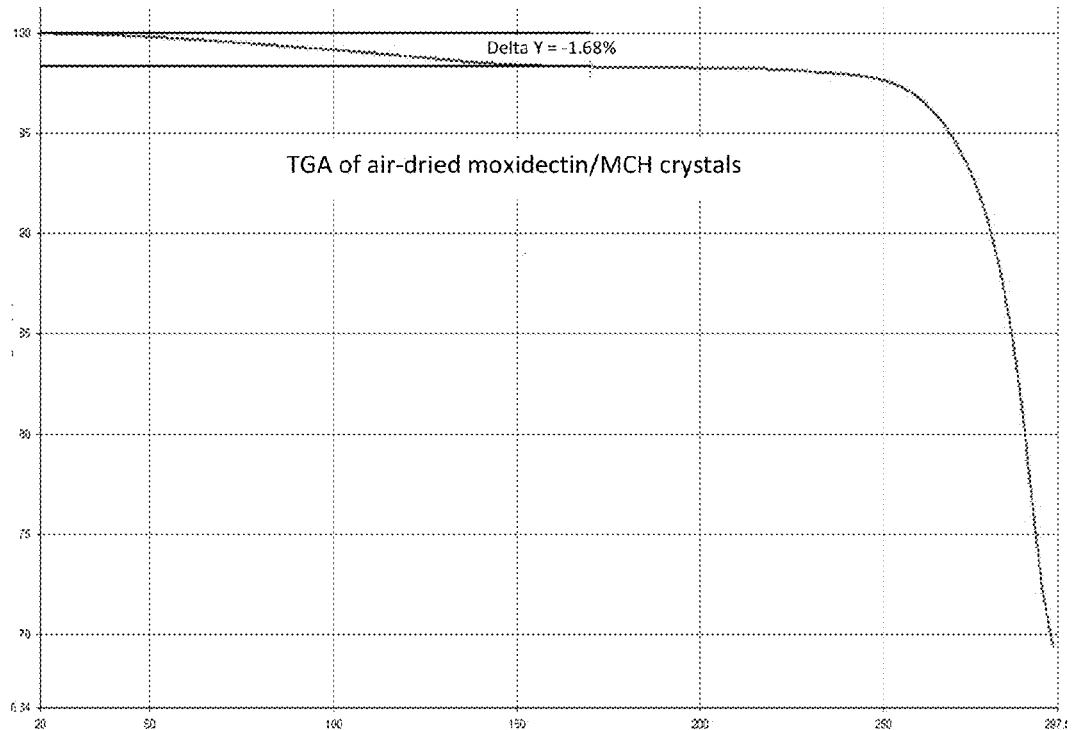
Figure 40:
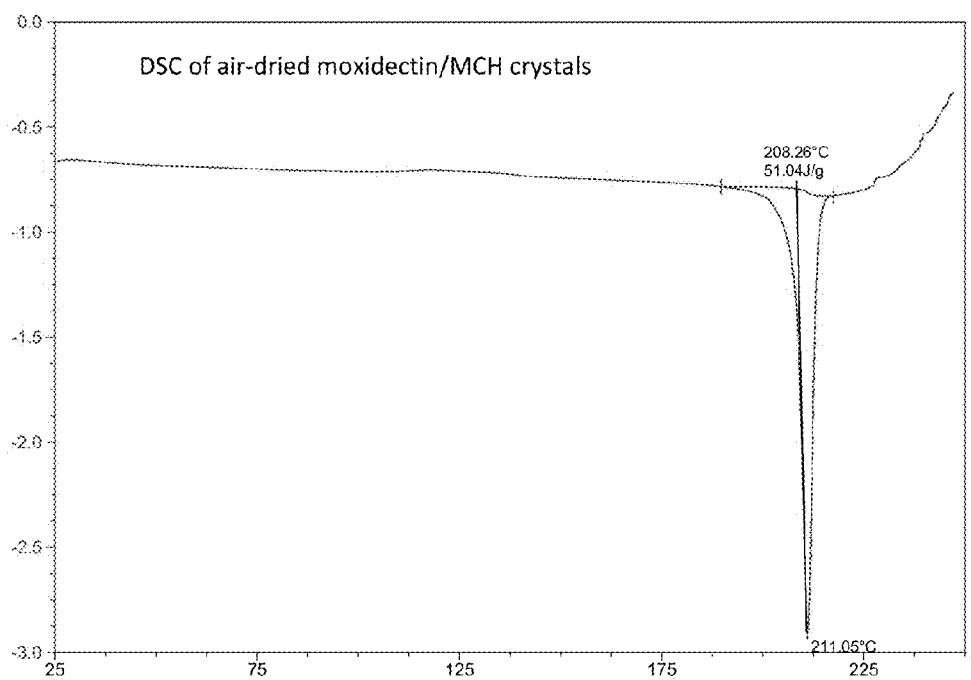
Figure 41:
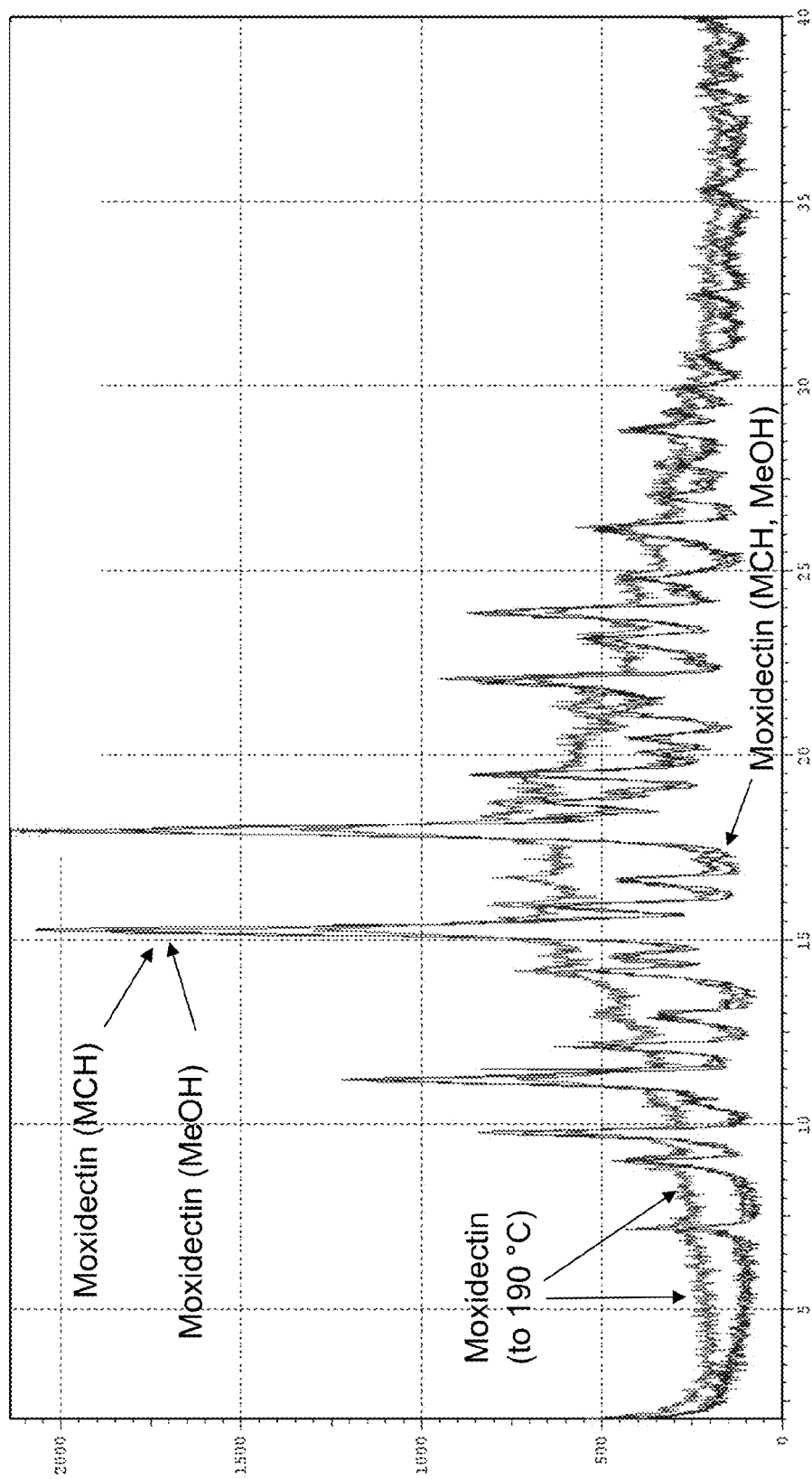

Thermal analysis of air-dried Moxdectin.MCH crystal demonstrated a weight loss of 1.68% upon heating from 50 to 150° C. (FIG. 39). The compound decomposes above 250° C. DSC demonstrated an apparent melting point at 211° C. (FIG. 40). This melting temperature is in agreement with that of the thermally transformed solid and Moxidectin MeOH, implying that they are the same crystalline form. Further, the PXRD patterns of the moxidectin crystals obtained from methanol and MCH are identical (FIG. 13 for MeOH vs. FIG. 41 for MCH) further confirming the similarity of the crystal forms from the two solvent systems Conclusions.

A series of crystalline moxidectin forms were obtained from alcohol solvents including methanol, ethanol, IPA and butanol etc. Those prepared from methanol and methylcyclohexane have essentially the same PXRD patterns as the thermally transformed one, indicating they have similar crystal form. Recrystallization of moxidectin from ethanol, IPA and n-butanol produce their respective solvates. The moxidectin EtOH and moxidectin.IPA solvates become amorphous after loss of solvents, while surprisingly and unexpectedly, the moxidectin n-butanol remains crystalline upon rapid removal of solvent. Crystalline moxidectin is almost non-hygroscopic, while amorphous moxidectin is slightly hygroscopic.

Example 2

Preparation of Slow-Release Polymeric Implants Comprising Moxidectin, and In Vitro Release Profiles Summary.

The crystal form properties of moxidectin API are depicted in FIGS. 2-8 and 10-12: including glass transition temperature, crystallization and the crystal melt. Polymeric implants containing either amorphous or crystalline moxidectin were prepared. For amorphous moxidectin implants, the process temperature was kept between ~120-170° C. Inventors envision that any temperature above 120° C. (but below moxidectin's decomposition temperature) would be acceptable as the moxidectin would flow above its glass transition temperature and would be more easily extruded with increasing temperature (i.e. from 120 to 170° C.). The inventors found surprisingly and unexpectedly that moxidectin crystallizes above 170° C. Thus, there is a narrow temperature range that is optimal for preparation of the inventive implants, and processing at a temperature higher than re-crystallization temperature, though it runs counter to expectation, is not desirable for producing implants containing amorphous moxidectin. When processed at temperatures between 180-210° C., amorphous moxidectin crystallizes, and this transition has the effect of altering the release profile of any polymeric implants produced.

Polymeric Implants.

Figure 43:
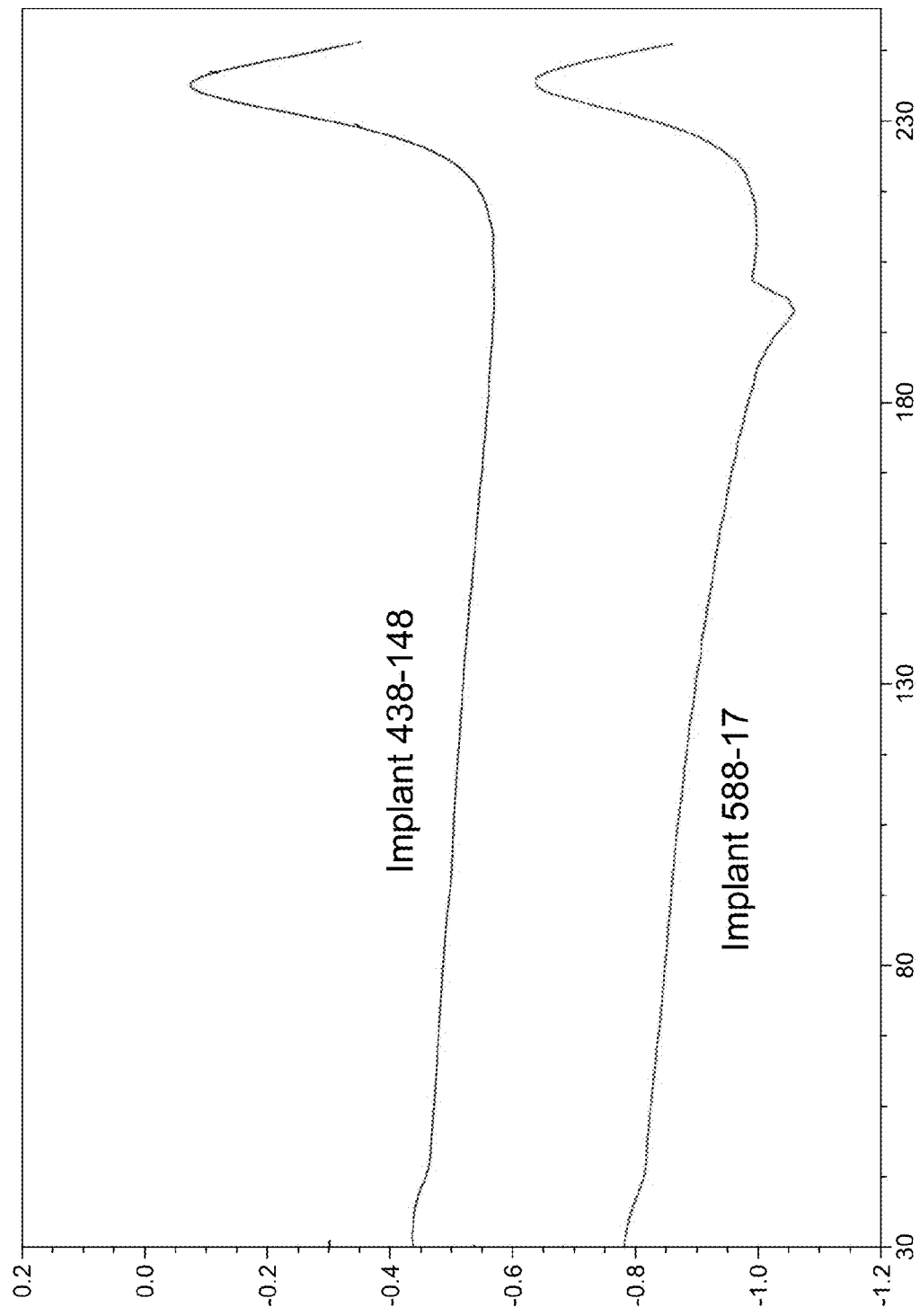
Figure 44:
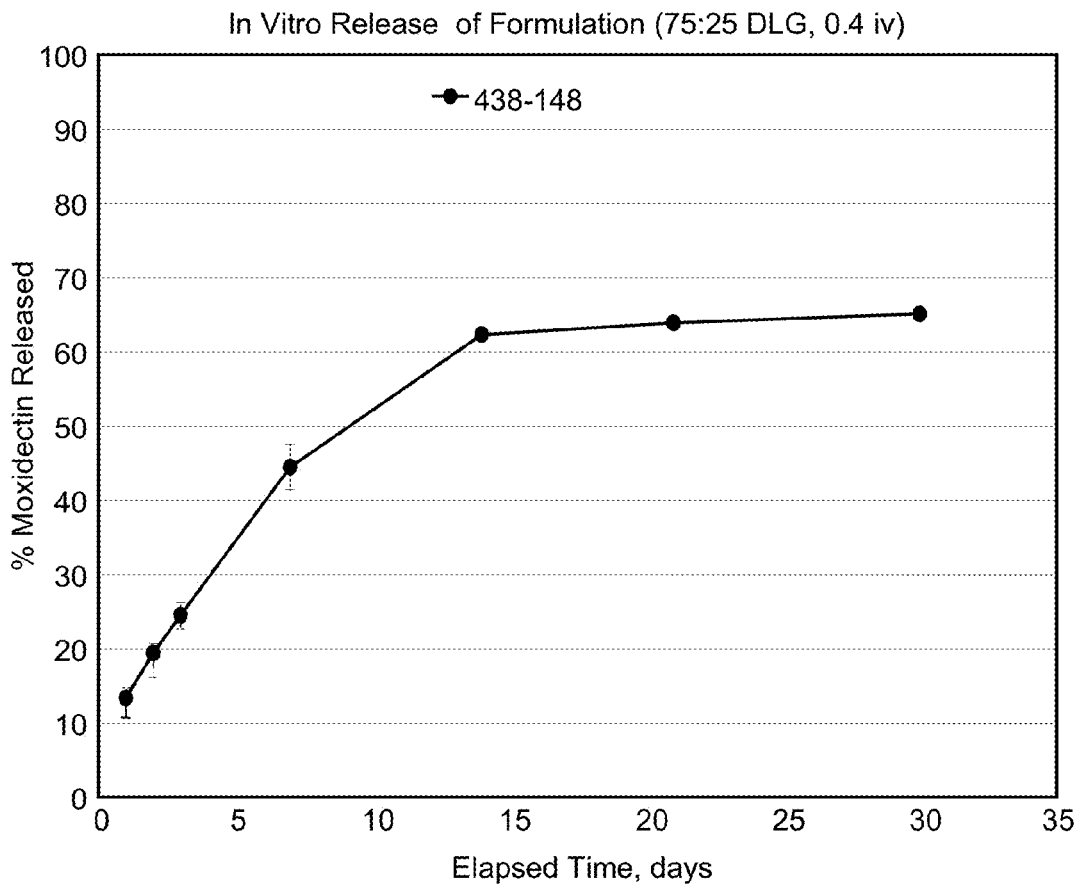

A solution of moxidectin (40% w/w), BHT (1.4%) and poly d lactide-glycolide (75:25 L:G; 0.4 iv) was prepared in methylene chloride and spray dried on a Buchi spray drier. The spray dried powder was placed in the Tenius Olsen plastometer and extruded at 118° C. The resulting ~0.8 mm diameter polymer strand was cut into small pellets ~2 mm in length. Five pellets were placed in a scintillation vial containing 10 mL 2% SDS in PBS, pH 7. Triplicate vials were prepared and placed in a 37° C. shaking (120 rpm) water bath. The solution was removed at each sampling point, replaced with fresh 2% SDS in PBS and assay by HPLC. The results are shown in FIG. 44. The in vitro release profile is provided in FIG. 44. Additionally, samples were assayed by DSC (FIG. 43). Moxidectin was amorphous in the pellet samples.

Figure 45:
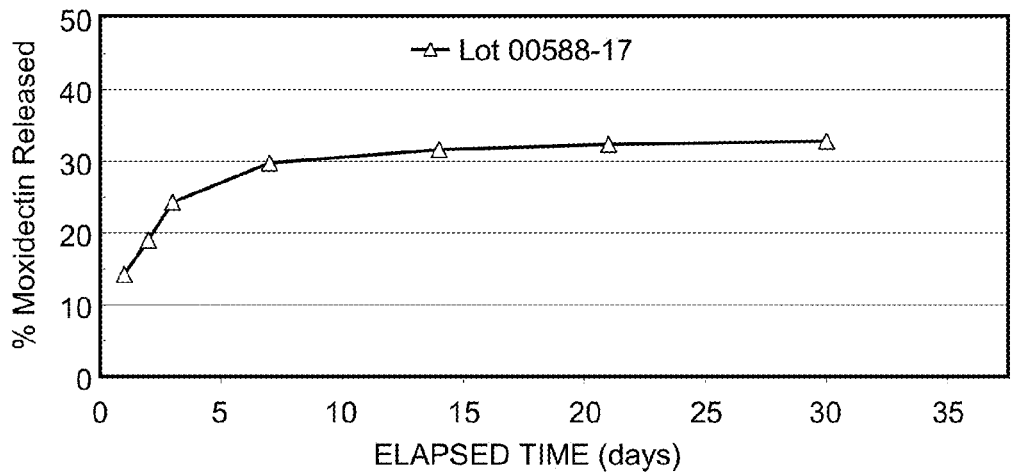

In an alternate batch, a solution of moxidectin (40% w/w), BHT (1.4%), and poly d lactide-glycolide (75:25 L:G; 0.4 iv) was prepared in methylene chloride and spray dried on a Buchi spray drier. The spray dried powder was placed in ⅜" single screw extruder (0.75 mm short land die, elongational mixing screw, K-Tron micro feeder set to 24 g/hr) and extruded at 130° C. The resulting ~0.8 mm diameter polymer strand was cut into small pellets ~2 mm in length. Five pellets were placed in a scintillation vial containing 10 mL 2% SDS in PBS, pH 7. Triplicate vials were prepared and placed in a 37° C. shaking (120 rpm) water bath. The solution was removed at each sampling point, replaced with fresh 2% SDS in PBS and assay by HPLC. The in vitro dissolution data are shown in FIG. 45.

Example 3

Moxidectin Plasma Profile in Canines Injected with Polymeric Implants

Figure 46:
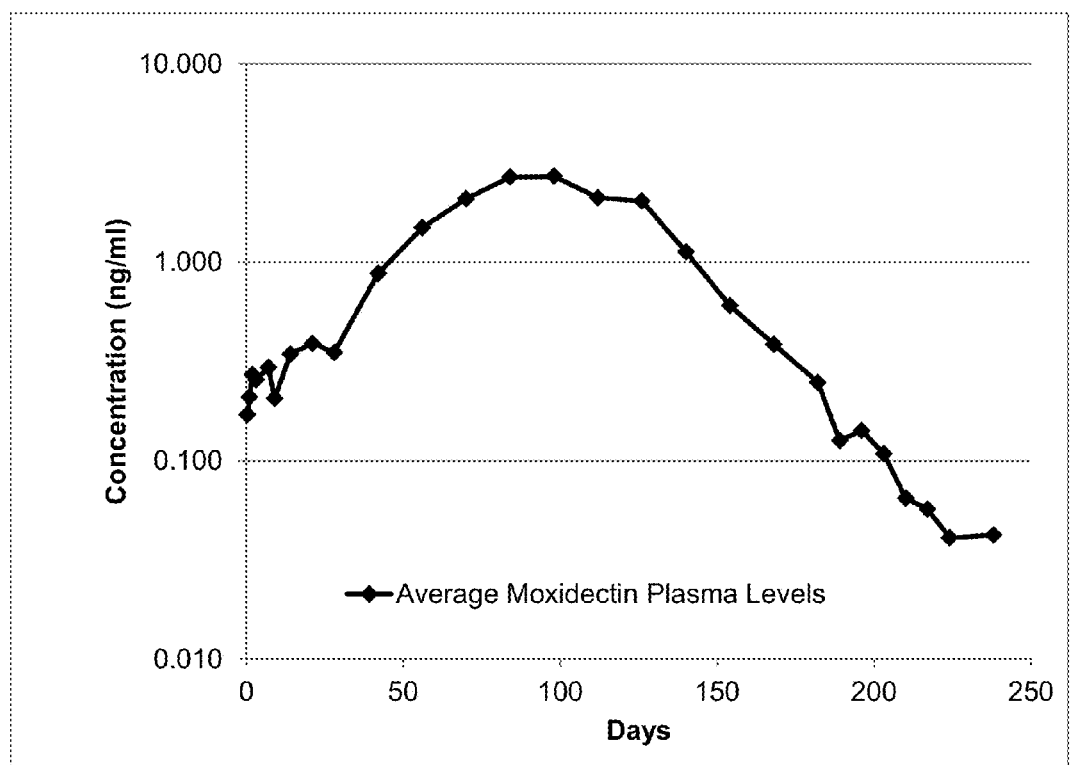

On Day 0, five canine animals were administered subcutaneously one injection of 4 implants (containing 2000 mcg amorphous moxidectin, 75:25 DLG (0.4 i.v.), prepared as above-lot#438-148), a separate implant needle containing the appropriate number of implants was used for each treated animal. Blood samples (approximately 5 to 7 mL) were collected in individually labeled heparinized tubes. Plasma was recovered and stored frozen in aliquots, until required for assay. Canine study data results are shown in FIG. 46. Additionally, implant samples were also assayed by DSC and IR which determined that Moxidectin was amorphous in the implant.

Having thus described in detail the preferred embodiments of the present invention, it is to be understood that the above description of the invention is intended to be illustrative and not limited to particular details set forth in the above description, as many apparent variations thereof are possible. Various changes or modifications in the embodiment described may occur to those skilled in the art. These variations, changes and modifications can be made without departing from the scope or spirit of the invention.

What is claimed is:

1. A long-acting polymeric implant for non-human animals comprising PLGA and amorphous moxidectin.
2. The implant of claim 1 wherein the PLGA has an L:G ratio of about 50-75% to about 25-50% L:G.
3. The implant of claim wherein the L:G ratio is 75:25.
4. The implant of claim 3 which is active against endoparasites for a period of greater than 3 months.
5. The implant of claim 4 which is active against endoparasites for a period of greater than 4 months.
6. The implant of claim 5 which is active against endoparasites for a period of greater than 6 months.
7. The implant of claim 1 wherein the endoparasites are heartworms.
8. The implant of claim 1 wherein the animals are cats or dogs or cattle.
9. A method of producing the implant of claim 1 comprising the steps of:
   a) producing a solution of moxidectin and PLGA in a suitable solvent;
   b) adding from 0-1% (w/w) antioxidant;
   c) removing the solvent using a suitable drying means;
   d) subjecting the dried material of step c to extrusion at a suitable temperature to produce polymer strands;
   e) cutting or otherwise reducing the size of the polymer strands, thereby producing the implant.
10. The method of claim 9 wherein the solvent is methylene chloride and the drying means is a Buchi spray drier.
11. The method of claim 9 wherein the extrusion is performed at a temperature suitable for retaining the moxidectin in an amorphous state.
12. The method of claim 11 wherein the extrusion is not performed above 180° C.
13. The method of claim 12 wherein the extrusion is performed at between about 110° C. and about 180° C.
14. The method of claim 13 wherein the extrusion is performed at about 118° C.

* * * * *